United States Patent
Kim et al.

(10) Patent No.: US 10,864,226 B2
(45) Date of Patent: Dec. 15, 2020

(54) USE OF MICRORNA-188-5P FOR TREATING ALZHEIMER'S DISEASE

(71) Applicant: SEOUL NATIONAL UNIVERSITY R&DB FOUNDATION, Seoul (KR)

(72) Inventors: Hye Sun Kim, Seoul (KR); Kihwan Lee, Ellicott City, MD (US); Hyunju Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 16/465,865

(22) PCT Filed: Apr. 6, 2017

(86) PCT No.: PCT/KR2017/003783
§ 371 (c)(1),
(2) Date: May 31, 2019

(87) PCT Pub. No.: WO2018/101550
PCT Pub. Date: Jun. 7, 2018

(65) Prior Publication Data
US 2019/0298754 A1    Oct. 3, 2019

(51) Int. Cl.
| A61K 31/713 | (2006.01) |
| A61P 25/28 | (2006.01) |
| A61K 31/7105 | (2006.01) |
| C12N 15/113 | (2010.01) |
| A61K 48/00 | (2006.01) |

(52) U.S. Cl.
CPC ........ *A61K 31/713* (2013.01); *A61K 31/7105* (2013.01); *A61K 48/00* (2013.01); *A61P 25/28* (2018.01); *C12N 15/113* (2013.01)

(58) Field of Classification Search
CPC .. A61K 31/713; A61K 31/7105; A61K 48/00; C12N 15/113; C12N 2310/141; C12N 2310/321; C12N 2310/3521; A61P 25/28
USPC .................... 435/6.1, 91.1, 91.31, 455, 458; 514/44 A; 536/23.1, 24.5
See application file for complete search history.

(56) References Cited

U.S. PATENT DOCUMENTS

| 9,301,969 B2 | 4/2016 | Roh et al. |
| 2016/0188791 A1 | 6/2016 | Disney et al. |

FOREIGN PATENT DOCUMENTS

KR    10-2012-0088009 A    8/2012

OTHER PUBLICATIONS

Lee et al, J. Neuroscience, vol. 32, No. 16, pp. 5678-5687. (Year: 2012).*
Lee et al, Nature Scientific Reports, 6:34433 (Oct. 6, 2016). (Year: 2016).*
Lee, K., et al.; "An Activity-Regulated microRNA, miR-188, Controls Dendritic Plasticity and Synaptic Transmission by Downregulating Neuropilin-2", The Journal of Neuroscience, Apr. 18, 2012, 32 (16), pp. 5678-5687.
Zhang, H., et al.; "miR-188-5p inhibits tumour growth and metastasis in prostate cancer by repressing LAPTM4B expression", Oncotarget, vol. 6, No. 8, 2015, pp. 6092-6104.
Lee, K., et al.; "Replenishment of microRNA-188-5p restores the synaptic and cognitive deficits in 5XFAD Mouse Model of Alzheimer's Disease", Scientific Reports, Oct. 6, 2016, pp. 1-14.
International Search Report from corresponding PCT Application No. PCT/KR2017/003783, dated Aug. 21, 2017.

* cited by examiner

*Primary Examiner* — Jane J Zara
(74) *Attorney, Agent, or Firm* — Harness, Dickey & Pierce, P.L.C.

(57) ABSTRACT

The present invention relates to a use of microRNA(miR)-188-5p which can be used for treatment of Alzheimer's disease, and the pharmaceutical composition comprising miR-188-5p as an active ingredient of the present invention can inhibit the expression of NRP2 protein when it is added to a subject having Alzheimer's disease, thereby restoring the reduced density of dendritic spines and enhancing synaptic transmission, and thus it can prevent or treat Alzheimer's disease effectively.

12 Claims, 39 Drawing Sheets

Specification includes a Sequence Listing.

USE OF MICRORNA-188-5P FOR TREATING ALZHEIMER'S DISEASE

FIELD

This application is a national phase application of PCT Application No. PCT/KR2017/003783, filed on Apr. 6, 2017, which claims the benefit and priority to Korean Patent Application No. 10-2016-0163785, filed on Dec. 2, 2016. The entire disclosures of the applications identified in this paragraph are incorporated herein by references. The present invention relates to a use of microRNA-188-5p which can be used for treatment of Alzheimer's disease.

BACKGROUND

Alzheimer's disease (AD) is a chronic neurodegenerative disease that accounts for 50 to 70% of dementia which causes cognitive impairment due to gradual degeneration of nerve cells. AD is characterized by accumulation of 39-43 amino acid peptides, termed Amyloid-beta (Amyloid-β, Aβ) in a form of a protofibril, present as amyloid plaques and amyloid in brain tissue. Deposition of Aβ in AD is harmful to nerve cells and interstitial cells in brain, resulting in brain inflammation and nerve cell apoptosis which are characteristics of AD.

In brain of patients who die from AD, senile plaques and neurofibrillary tangles appear as pathological features. Among them, senile plaques are formed by accumulation of proteins and dead cells and the like on the outside of cells, and its main constituent is Aβ peptide. The gradual loss of cognitive function, a main feature of AD patients seems to be caused by abnormally accumulated Aβ. Aβ is produced through a proteolysis process from an amyloid precursor protein (hereinafter, referred to as "APP"). The precursor, APP is degraded by β-secretase (BACE) and γ-secretase, thereby producing Aβ.

MicroRNAs are non-coding RNA molecules with a length of approximately 22 nucleotides, which serve as post-transcriptional regulators of gene expression. In the central nervous system, microRNAs have been shown to regulate development, survival, function and plasticity. MicroRNAs and their precursors exist in synaptic fractions along with components of the microRNA machinery, where they are poised to regulate neurotransmission. Furthermore, dysfunction of microRNAs within neurons and alterations in microRNA expression have been associated with the pathogenesis of neurodegenerative diseases such as AD. However, little is known regarding whether restoring or reversal of deregulated microRNAs is capable of counteracting deficits in cognitive or synaptic dysfunctions in AD.

Since AD-mediated cognitive deficits have been postulated as synaptic by origin, one area that has been extensively researched is the study of aberrant amyloid beta peptide$_{1-42}$ (Aβ$_{1-42}$)-mediated modulation of synaptic transmission and plasticity. The most extensively documented synaptic phenomenon in this regard is long-term potentiation (LTP), which is inhibited by overexpression of APP genes and Aβ administration.

Nrp-2 has been previously reported to serve as a negative regulator of spine development and synaptic structure, together with its ligand, semaphorin-3F (Sema-3F). Nrps are 130 to 140 kDa single transmembrane spanning glycoproteins that function as receptors for class 3 semaphorins, polypeptides essential for axonal guidance and for members of the vascular endothelial growth factor (VEGF) family, angiogenic cytokines.

AD is a disease caused by damage to nerve cells and synapses, and no fundamental therapeutic agent has been developed to date. It is not clear yet whether the increase of dendritic density of nerve cells and recovery of synaptic damage are related to microRNAs for treating AD, and it is necessary to develop an effective AD therapeutic agent using a specific microRNA.

SUMMARY

Technical Problem

A problem to be solved by the present invention is to provide a use of microRNA-188-5p (miR-188-5p) for preventing or treating Alzheimer's disease (AD). In addition, a problem to be solved by the present invention is to provide a method for preventing or treating AD using the miR-188-5p.

Technical Solution

The inventors of the present invention have made extensive efforts to develop a therapeutic agent for Alzheimer's disease (AD), and as a result, it has been surprisingly found that when a specific microRNA reduced in a patient or an animal having AD is supplemented, cognitive function and synaptic transmission damage is restored to the normal level, thereby completing the present invention.

More specifically, the present inventors found that the expression of microRNA-188-5p (miR-188-5p) in the brain tissue of AD patient and transformed mouse (5×FAD) is down-regulated. In addition, the present inventors found that oligomer Aβ$_{1-42}$ treatment reduced the miR-188-5p expression in the primary hippocampal neuron culture and the miR-188-5p solved Aβ$_{1-42}$-mediated synapse removal and synaptic function disorders. In the primary hippocampal neuron which was cultured from 5×FAD mouse and treated with oligomer Aβ$_{1-42}$, addition of miR-188-5p restored the reduction of the dendritic density. Moreover, it was shown that disorders of cognitive function and synaptic transmission of 5×FAD mouse was alleviated, through virus-mediated miR-188-5p expression. In conclusion, through the experimental results that the administration of miR-188-5p increased the dendritic density of nerve cells of the AD animal model and restored synaptic damage, the present inventors found that miR-188-5p could be effectively used for preventing or treating AD.

In one aspect, the present invention provides a pharmaceutical composition for preventing or treating Alzheimer's disease comprising miR(microRNA)-188-5p as an active ingredient. The pharmaceutical composition of the present invention can restore the reduced mature miR-188-5p to the normal level in an AD patient or animal model, thereby restoring damage of synaptic function or cognitive function in the AD patient or animal model. In other words, the pharmaceutical composition of the present invention increases the density of dendritic spines and enhances synaptic plasticity, thereby restoring learning and memory deterioration by AD, as miR-188-5p inhibits the expression of NRP2 protein, more specifically, as miR-188-5p inhibits Nrp2 mRNA to be translated into a protein by binding to 3'-UTR region of Nrp2 mRNA.

In another aspect, the miR-188-5p which is the active ingredient of the pharmaceutical composition for preventing or treating Alzheimer's disease of the present invention may consist of the sequence represented by SEQ ID NO: 1

(miRbase accession number MIMAT0005301). The sequence of SEQ ID NO: 1 represents the mature miR-188-5p sequence.

In other aspect, the pharmaceutical composition for preventing or treating Alzheimer's disease of the present invention may comprise a pre-miRNA (precursor) of miR-188-5p. The pre-miRNA of miR-188-5p may consist of the sequence represented by SEQ ID NO: 3. The sequence of the pre-miRNA of miR-188-5p (SEQ ID NO: 3) may comprise not only the mature miR-188-5p (SEQ ID NO: 1) but also a loop sequence (TCTC) and a complementary sequence to miR-188-5p (SEQ ID NO: 2). The SEQ ID NO: 3 is a sense sequence of the pre-miRNA of miR-188-5p, and its antisense sequence may consist of the sequence represented by SEQ ID NO: 4.

The sequences of SEQ ID NOs: 1 to 4 are shown in the following Table 1 and FIG. 8.

ing miR-188-5p as an active ingredient. In addition, the present invention provides a composition for restoring cognitive function comprising miR(microRNA)-188-5p as an active ingredient. Furthermore, the present invention provides a method for restoring deterioration of synaptic transmission function or cognitive function related to Alzheimer's disease by adding miR-188-5p to a subject.

In other aspect, the present invention provides a use of miR-188-5p for preventing or treating Alzheimer's disease. Specifically, the use may be used as a use for restoring deterioration of synaptic transmission function or cognitive function related to Alzheimer's disease by adding miR-188-5p to a subject.

In other aspect, the present invention provides a use of miR-188-5p for preparing a medicament for preventing or treating Alzheimer's disease. The miR-188-5p of the present invention may be used as an active ingredient of a medica-

TABLE 1

| SEQ ID NO: | Characteristics | Sequence |
| --- | --- | --- |
| 1 | Mature miR-188-5p sequence | CATCCCTTGCATGGTGGAGGG |
| 2 | miR-188-5p complementary sequence | CCCTCCACCATGCAAGGGATG |
| 3 | Sense of pre-miRNA of miR-188-5p | 5'-AAC G CATCCCTTGCATGGTGGAGGG TCTC CCCTCCACCATGCAAGGGATG TTTTTT C-3' |
| 4 | Antisense of pre-miRNA of miR-188-5p | 5'-TCGA G AAAAAA CATCCCTTGCATGGTGGAGGG GAGA CCCTCCACCATGCAAGGGATG C GTT-3' |

In other aspect, the pharmaceutical composition for preventing or treating Alzheimer's disease of the present invention may comprise an expression vector containing a polynucleotide encoding miR-188-5p. Specifically, the expression vector may be added to a mammal to express mature miR-188-5p in a mammal cell.

In the present invention, the expression vector may be a lentivirus vector into which the miR-188-5p sequence is subcloned. In addition, the expression vector may be a lentivirus vector into which the pre-miRNA (precursor) sequence of miR-188-5p or its sense and antisense sequence is subcloned.

In one example, the expression vector for miR-188-5p may use pLentiLox3.7 vector as a backbone vector. As the expression vector, pLL3.7-miR-188-DsRed2, which is prepared by constructing pLL3.7-miR-188-EGFP vector using miR-188-5p and its complementary sequence in the backbone vector and then introducing the complementary sequence to pLL3.7-DsRed2 vector, may be used.

In other aspect, the present invention provides a host cell comprising an expression vector containing a polynucleotide encoding miR-188-5p.

In other aspect, the present invention provides a kit for preventing or treating Alzheimer's disease comprising the pharmaceutical composition for preventing or treating Alzheimer's disease.

In other aspect, the present invention provides a method for preventing or treating Alzheimer's disease by adding miR-188-5p to a subject. The method for preventing or treating Alzheimer's disease of the present invention may comprise a step of adding an expression vector containing a polynucleotide encoding miR-188-5p to a subject.

In other aspect, the present invention provides a composition for restoring synaptic transmission function comprisment for preventing or treating AD. The medicament may comprise mature miR-188-5p, a pre-miRNA (precursor) of miR-188-5p or an expression vector containing miR-188-5p and the like as an active ingredient, and it is not limited in any form as long as miR-188-5p can be normally expressed in a subject.

The pharmaceutical composition for preventing or treating Alzheimer's disease of the present invention may be formulated suitably for a route to be administered. The composition may be administered for example, via parenteral administration such as intravenous, in blood, subcutaneous, inhalation, percutaneous (local), mucosal or rectal, intramuscular, intraarterial and intranasal, and the like, or oral administration route.

In the present invention, miR-188-5p may be used as itself or may be used in a form of pharmaceutically acceptable acid addition salts or metal complexes, for example, salts such as zinc, iron and the like. More specifically, as the acid addition salt, hydrogen chloride, hydrogen bromide, sulphate, phosphate, maleate, acetate, citrate, benzoate, succinate, malate, ascorbate or tartrate, and the like may be used. In addition, the composition containing miR-188-5p or its salt form as an active ingredient may mix and dilute the active ingredient with a pharmaceutically acceptable carrier, or enclose it in a container-shaped carrier, according to the administration method, administration form, and therapeutic purpose, by a common method.

When the carrier is used as a diluent, it may be prepared in a form like powder, granule, injection, syrup, solution, tablet, suppository, pessaries, ointment, cream or aerosol and the like for oral administration and parenteral administration using one or more kinds of carriers selected from the group consisting of salt water, buffer, dextrose, water, glycerol, Ringer's solution, lactose, sucrose, calcium silicate, methyl cellulose and ethanol, and so on.

It may be formulated so as to provide rapid, persistent or delayed release of the active ingredient after administration into a mammal by further comprising a filler, anti-coagulant, lubricant, flavoring, emulsifier or preservative, and the like to the formulation. In addition, the dosage of the present invention is not limited as it may be adjusted according to the condition of patients, administration route and administration form, and depending on symptoms, those skilled in the art can obviously use it within a variety of range. Commonly, in the present invention, as the experimentally effective dose, 0.0001 to 100 mg per 1 kg body weight a day may be continuously or intermittently administered.

Advantageous Effects

The pharmaceutical composition comprising miR-188-5p as an active ingredient of the present invention can inhibit the expression of NRP2 protein when it is added to a subject having Alzheimer's disease, thereby restoring the reduced density of dendritic spines and enhancing synaptic transmission, and thus it can prevent or treat Alzheimer's disease effectively.

BRIEF DESCRIPTION OF THE DRAWINGS

FIG. 1 is a drawing which shows that miR-188-5p was significantly down-regulated in the brains from AD patients.

FIG. 2 is a drawing which shows that Oligomeric Aβ1-42 reduced the expression of miR-188-5p.

FIG. 3 is a drawing which shows that miR-188-5p restored the reduction in dendritic spine density and basal synaptic transmission induced by oligomeric Aβ$_{1-42}$.

FIG. 3l: A graph shows the result of experimenting the 2'-O-methyl (2'-O-Me) to miR-188-5p or miR-188-3p on mEPSC.

FIG. 4 shows that miR-188-5p rescued the reduction in dendritic spine density in primary hippocampal neurons cultured from P1 5×FAD mice.

FIG. 5 shows that miR-188-5p rescued the memory deficits by restoring synaptic dysfunction in 5×FAD mice.

FIG. 5d: Sample traces of synaptic responses at the SC-CA1 synapse with various stimulation intensities in each group.

FIG. 5e: The relationship between fEPSP slope and FV amplitude in each group (n=1~6 slices from 4 mice for each group).

FIG. 5f: The FV amplitudes were plotted against stimulation intensities.

FIG. 5g: Representative traces of fEPSP responses during baseline and 51-55 min after 4× TBS in each group (up). LTP induced by 4× TBS at SC-SC1 synapses (bottom). Each point represents mean fEPSP slope normalized to the average baseline response before TBS.

FIG. 5h: Summary of the magnitude of mean LTP during 51-55 min after TBS relative to baseline in each group (wild-type, n=1-6 slices from 4 mice for each group; wild-type/188-5p, n=12; 5×FAD, n=8; 5×FAD/188-5p, n=10). All data represent the mean±SEM of mice pooled from 4 mice for each group. **$p<0.01$ compared to control virus injected wild-type mice, #$p<0.0001$ compared to control virus injected 5×FAD mice by non-parametric Mann-Whitney test. TBS=theta-burst stimulation, FV=fiber volley.

FIG. 6 shows that CREB regulates miR-188 expression.

DETAILED DESCRIPTION

Hereinafter, the present invention will be described in detail with examples, and the like to facilitate understanding of the present invention. However, examples according to the present invention may be modified into various other forms, and the scope of the present invention should not be construed as being limited to the following examples. The examples of the present invention are provided to more fully explain the present invention to those skilled in the art.

Example 1: Reduction of miR-188-5p in Brain Tissues from AD Patients

The expression of miR-188-5p was examined using in the brain tissues of AD patients and age-matched control subjects by employing real-time quantitative PCR (RT-qPCR). Detailed information on the age-matched control subjects and AD patients used in this study is shown in Table 2.

TABLE 2

| Name | NBB Number | Autopsy Number | Code | Sex | Age | Anatomical region |
|---|---|---|---|---|---|---|
| cerebral cortex-control #1 | 00-032 | S00/059 | 100 | K1 | F | 78 | medial frontal gyrus |
| cerebral cortex-control #2 | 99-100 | S99/214 | 100 | K1 | M | 79 | medial frontal gyrus |
| cerebral cortex-control #3 | 02-024 | S02/055 | 300 | GFM2 | F | 75 | medial frontal gyrus |

TABLE 2-continued

| Name | NBB Number | Autopsy Number | Code | Sex | Age | Anatomical region |
|---|---|---|---|---|---|---|
| cerebral cortex-Alzheimer's disease#1 | 98-015 | S98/028 | 234 | A2 | F | 87 | medial frontal gyrus |
| cerebral cortex-Alzheimer's disease#2 | 00-054 | S00/115 | 300 | GFM1 | M | 59 | medial frontal gyrus |
| cerebral cortex-Alzheimer's disease#3 | 03-017 | S03/042 | 300 | GFM2 | M | 67 | medial frontal gyrus |
| cerebral cortex-Alzheimer's disease#4 | 04-068 | S04/0232 | 300 | GFM2 | F | 72 | medial frontal gyrus |
| cerebral cortex-Alzheimer's disease#5 | 00-091 | S00/194 | 300 | GFM2 | F | 76 | medial frontal gyrus |
| hippocampus-control#1 | 00-032 | S00/059 | 100 | D3 | F | 78 | hippocampus |
| hippocampus-control#2 | 99-100 | S99/214 | 100 | D3 | M | 79 | hippocampus |
| hippocampus-control#3 | 02-024 | S02/055 | 300 | HIP2 | F | 75 | hippocampus |
| hippocampus-Alzheimer's disease#1 | 98-015 | S98/028 | 234 | B1 | F | 87 | hippocampus |
| hippocampus-Alzheimer's disease#2 | 00-054 | S00/115 | 300 | HIP1 | M | 59 | hippocampus |
| hippocampus-Alzheimer's disease#3 | 03-017 | S03/042 | 300 | HIP2 | M | 67 | hippocampus |
| hippocampus-Alzheimer's disease#4 | 04-067 | S04/232 | 300 | HIP3 | F | 72 | hippocampus |
| hippocampus-Alzheimer's disease#5 | 01-076 | S01/173 | 300 | HIP3 | M | 75 | hippocampus |

Figure 1A:
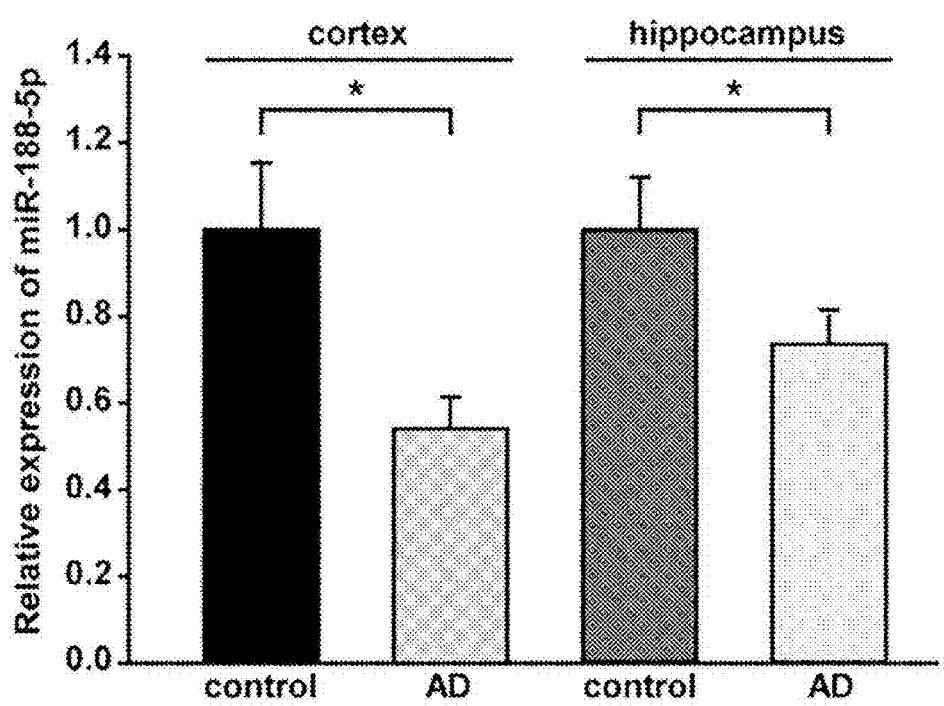
FIG. 1a: miR-188-5p expression was examined by RT-qPCR in brains from AD patients and age-matched control subjects. miR-188-5p expression was significantly down-regulated in cerebral cortices (n=3, vs. age-matched control subjects, n=4, Mann-Whitney test) and hippocampi (n=6, vs. age-matched control subjects, n=4, Student's t-test) of AD patients.
Figure 1B:
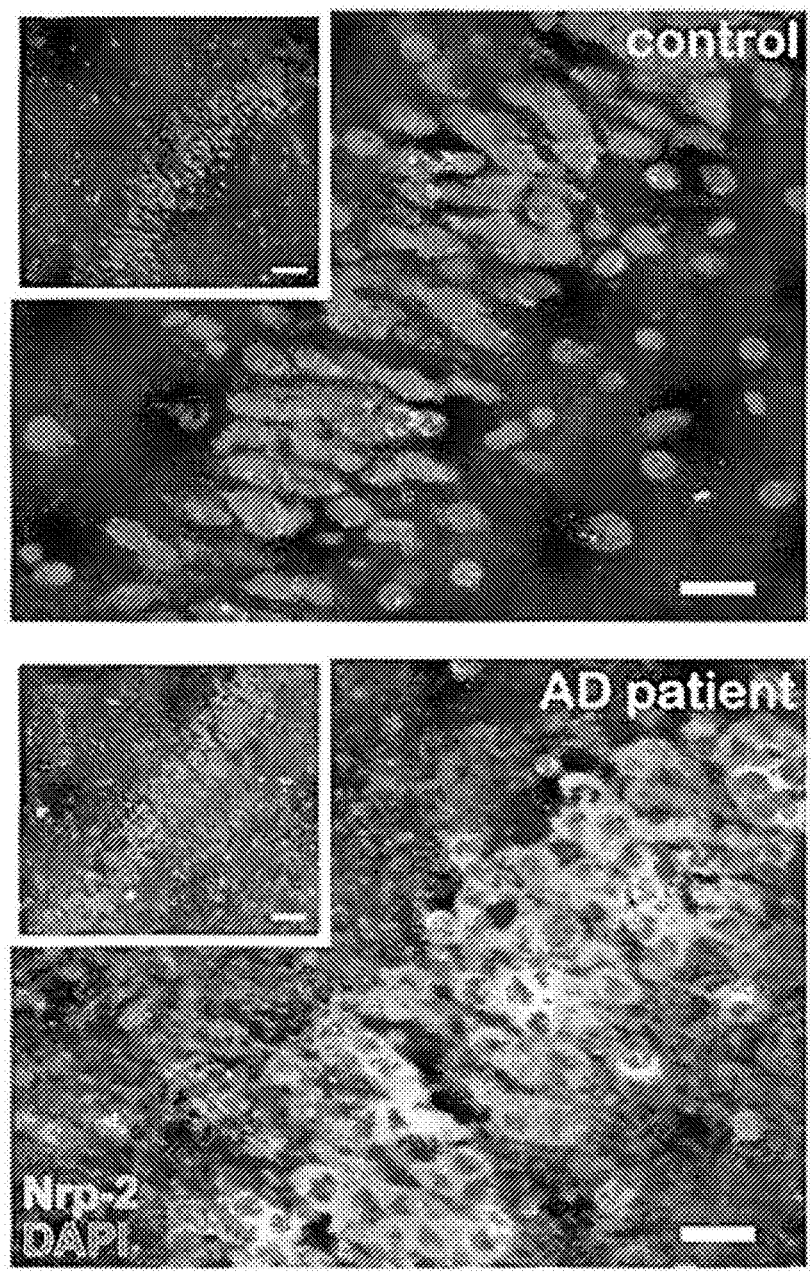
FIG. 1b: Representative images of the dentate gyrus of AD patients (98-year-old) compared with an age-matched control subjects. Nrp-2 immunoreactivity was measured by immunohistochemistry. Scale bars, 50 μm (inset, white square box) and 20 μm (magnified panel).
Figure 1C:
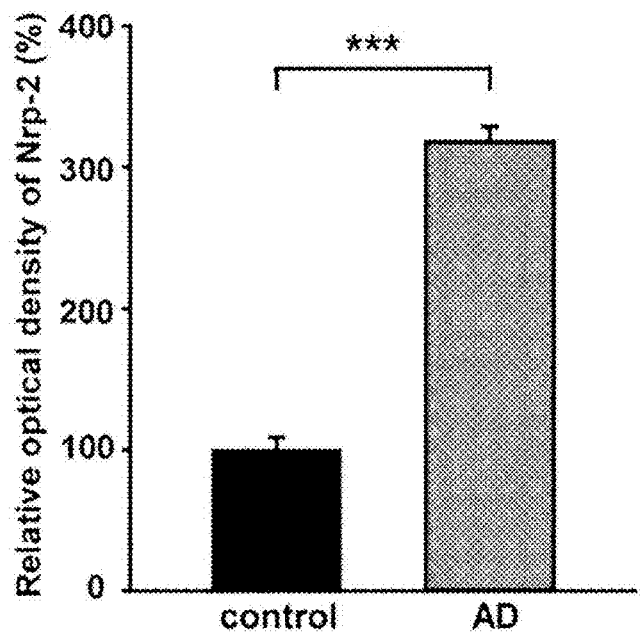
FIG. 1c: Quantitative graphs for Nrp-2 immunoreactivity in age-matched control subjects and AD (n=3, Mann-Whitney test) and hippocampi (n=4, Student's t-test). Data are represented as the mean±SEM. *p<0.05, ***p<0.001 compared to age-matched control subjects.

Information on the control subjects and Alzheimer's disease patients. A human sample stock list from the cerebral cortices and hippocampi of control subjects and AD patients. NBB=Netherlands brain bank.

miR-188-5p expression was significantly down-regulated in the cerebral cortices (0.54±0.07, p=0.013) and hippocampi (0.74±0.05, p=0.038) of AD patients (FIG. 1a). Moreover, the immunoreactivity against Nrp-2, one of the molecular targets for miR-188-5p, was markedly increased (318.02±10.86%, p<0.001; FIG. 1b,c) in the hippocampi of AD patients compared with age-matched control subjects.

Example 2: Reduction of the Expression of miR-188-5p by Oligomeric $A\beta_{1-42}$ $A\beta$, which is the main component of neuritic plaques in AD brains, is thought to be a causative factor in the pathogenesis of the disease23. Among several aggregated forms of $A\beta$ observed in AD brains, oligomeric $A\beta$ has been reported to play the most important role in disconnecting the synaptic network.

The effects of oligomeric $A\beta_{1-42}$ on miR-188-5p expression and the protein level of Nrp-2, the molecular target of miR-188-5p in rat primary hippocampal neurons were examined. Treatment with 5 µM oligomeric $A\beta_{1-42}$ for 24 h significantly decreased miR-188-5p expression (0.52±0.13 vs. vehicle-treated group, p=0.03, n=11, FIG. 2a), but increased Nrp-2 protein in the neurons (1 µM oligomeric $A\beta_{1-42}$ for 24 h, 1.30±0.36, p>0.05 vs. vehicle-treated group; 5 µM oligomeric $A\beta_{1-42}$ for 24 h, 2.38±0.85, p=0.037 vs. vehicle-treated group, FIG. 2b,c).

It was confirmed that the treatment with 5 µM oligomeric $A\beta_{1-42}$ for 24 h showed no significant difference in LDH release compared with vehicle treatment using a LDH assay (data not shown). Monomeric $A\beta_{1-42}$ significantly increased miR-188-5p (2.01±0.28 vs. vehicle treated group, p=0.02) in the neurons, which was not consistent with our expectations.

Figure 2A:
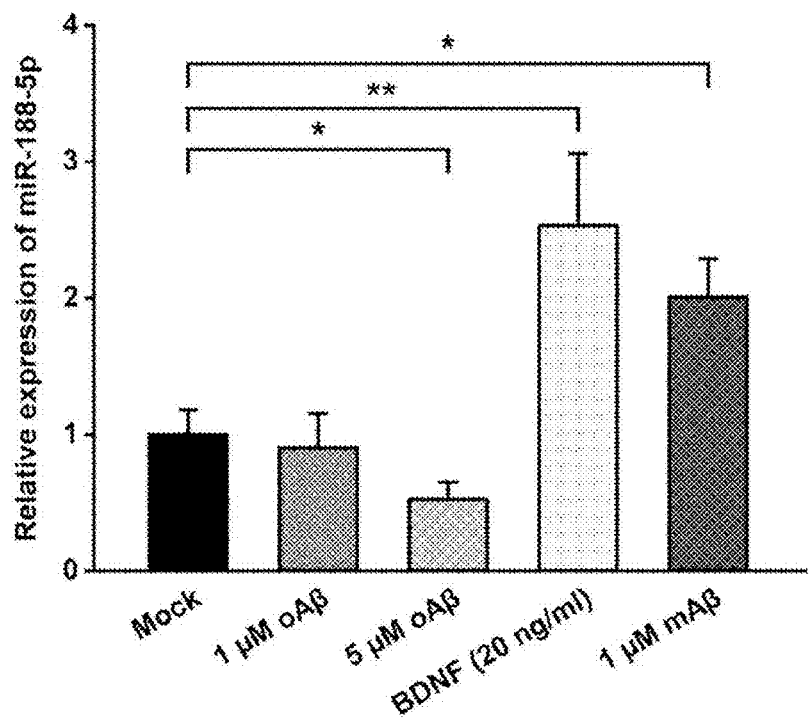
FIG. 2a: miR-188-5p expression was examined by RT-qPCR after treatment with oAβ in primary hippocampal neuron cultures. miR-188-5p expression was significantly reduced by treatment with 5 μM oAβ (n=11, Mann-Whitney test) compared to vehicle-treated controls.
Figure 2B:
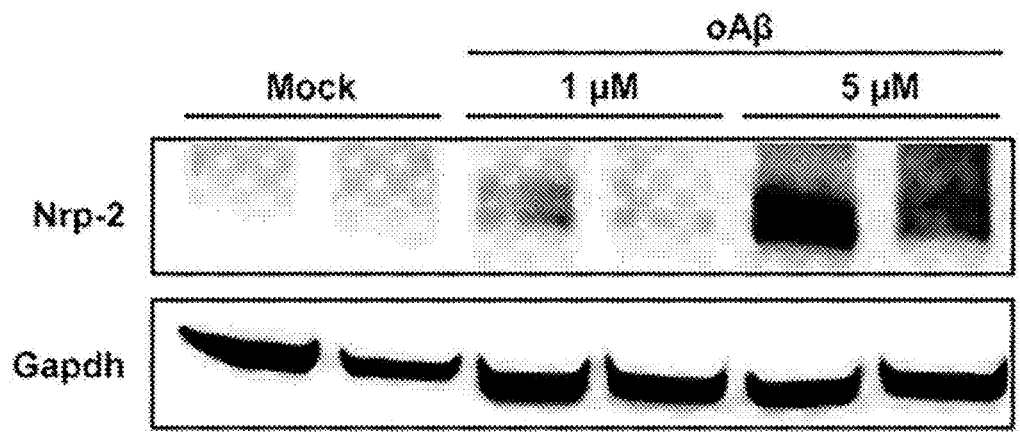
FIG. 2b: The Nrp-2 protein level was determined in primary hippocampal neuron after oAβ treatment by western blot (1 μM oAβ treatment and 5 μM oAβ treatment for 24 h compared with the control).
Figure 2C:
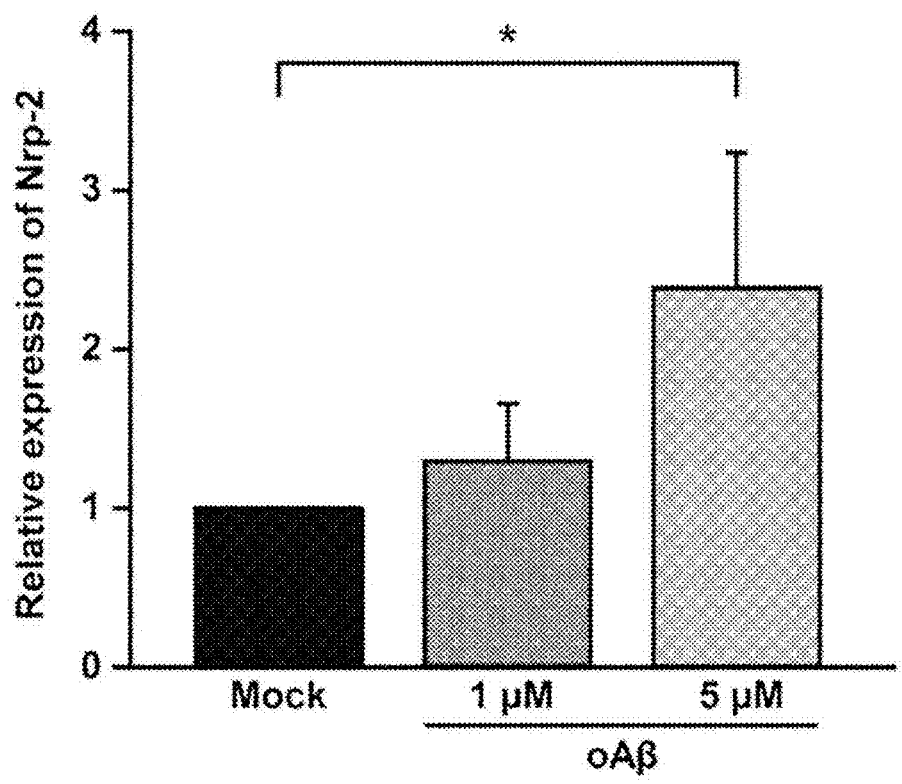
FIG. 2c: Quantitative graphs show relative quantification of Nrp-2 protein level normalized to Gapdh (internal control) after 24 h with 1 μM oAβ treatment (n=3) or 5 μM oAβ treatment (n=3, one-way ANOVA), compared to control (Mock). Data are represented as the mean±SEM. *p<0.05 compared to Mock. oAβ=oligomeric amyloid beta peptide$_{1-42}$, mAβ=monomeric amyloid beta peptid$_{1-42}$.

It was determined whether brain-derived neurotrophic factor (BDNF) affected miR-188-5p expression in the neuron cultures. BDNF is a neurotrophic factor that plays a pivotal role in synaptic plasticity and cognition. Recently, it has been suggested that a decrease in BDNF within the prefrontal cortex and hippocampus is related to cognitive deficits in AD animal models. Treatment with BDNF (20 ng/ml) significantly up-regulated miR-188-5p expression (2.53±0.53 vs. vehicle treated group, p=0.03; FIG. 2a).

Example 3: Restoring of $A\beta$-Mediated Reduction in Dendritic Spine Density and Basal Synaptic Transmission by miR-188-5p Aggregation of oligomeric $A\beta$ is thought to be a key pathophysiology and has been reported to play the most important role in neurotoxicity and neurodegeneration in AD. Dendritic spine and synapse loss are well documented in AD. It has been reported that $A\beta$ decreases dendritic spine density in primary neurons. In addition, the decrease in dendritic spine density was observed in the brains of AD animal model such as 5xFAD.

It was confirmed that the treatment with 5 µM oligomeric $A\beta_{1-42}$ for 24 h induced a significant reduction in dendritic spine density at DIV 17 in rat primary hippocampal neuron cultures. However, transfection with the miR-188-5p restored the $A\beta_{1-42}$-mediated reduction in dendritic spine density to the similar level of vehicle-treated group. The transfection of miR-scrambled (miR-SC) or miR-124, which is enriched in the brain, but does not target Nrp-2, did not affect $A\beta_{1-42}$-induced reduction in dendritic spine density (FIG. 3a-g). 9-10 neurons were analyzed for each group.

The numbers of dendrites analyzed per neuron is 4.90±0.64 (mock), 3.13±0.30 (1 µM oligomeric $A\beta_{1-42}$), 4.43±0.37 (5 µM oligomeric $A\beta_{1-42}$), 3.67±0.41 (miR-188+5 µM oligomeric $A\beta_{1-42}$), 4.67±0.67 (miR-124+5 µM oligomeric $A\beta_{1-42}$), 6.25±0.84 (miR-SC+5 µM oligomeric $A\beta_{1-42}$). These results suggest that the decrease in miR-188-5p expression causes down-regulation of dendritic spine density.

Next, mEPSCs (miniature excitatory postsynaptic current) was recorded and the frequency and amplitude to measure basal synaptic transmission were analyzed. A single whole-cell recording method was employed to record vehicle-treated or 5 µM $A\beta_{1-42}$-treated rat primary hippocampal neurons transfected with IRES-mGFP plus microRNA oligonucleotides (FIG. 3h-k). mEPSC frequency in $A\beta_{1-42}$-treated rat primary hippocampal neurons was significantly decreased compared to vehicle-treated neurons. However, in neurons treated with $A\beta_{1-42}$ plus 50 nM or 100 nM miR-188-5p oligonucleotides, the reduction in mEPSC frequency was almost completely reversed back to control levels. Again, this was a miR-188-5p-specific effect as neurons treated with $A\beta_{3-42}$ after co-transfection of miR-SC or miR-124 showed no effect on the attenuation of the $A\beta_{1-42}$-mediated reduction in mEPSC frequency.

The effects of 2'-O-methyl (2'-O-Me) oligonucleotide for miR-188-5p (2'-O-Me-188-5p-AS), which serves as a miR-188-5p specific inhibitor on mEPSCs were examined. First, the effects of 2'-O-Me-188-5p-AS on the level of miR-188-5p and miR-188-3p was examined, respectively. It was found that the level of miR-188-5p was significantly decreased by the treatment with 2'-O-Me-miR-188-5p AS for 6 days, while that of miR-188-3p did not show a significant change, indicating that 2'-O-Me-188-5p-AS serves as miR-188-5p specific inhibitor (FIG. 3l).

Figure 3A:
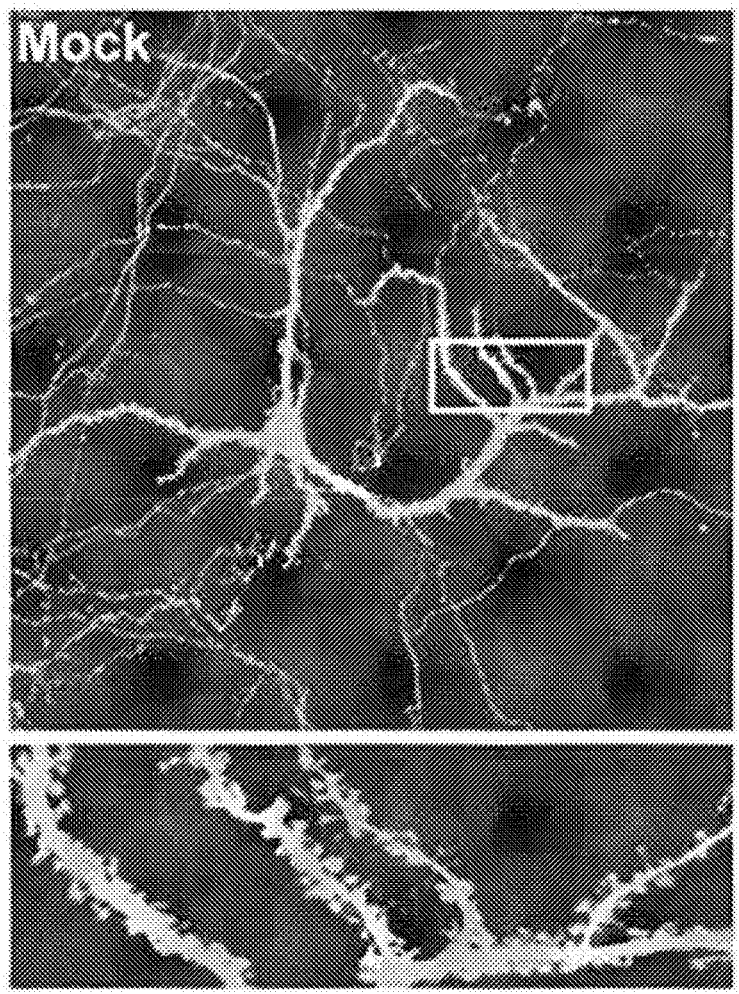
FIGS. 3a, 3b, 3c, 3d, 3e and 3f: Representative confocal images of dendritic spines in rat primary hippocampal neurons at DIV 18-20 after treating with oligomeric Aβ 1-42 (oAβ) for 24 h either alone or plus transfection with miR-188-5p (IRES-DsRed2), miR-124 or miR-SC oligonucleotides and the IRES-mGFP vector at DIV 10-12. The dendritic segment, outlined with a white box (upper), is magnified to delineate spine morphology (bottom). The scale bars indicate 20 μm (low-scaled panel) and 5 μm (magnified panel).
Figure 3B:
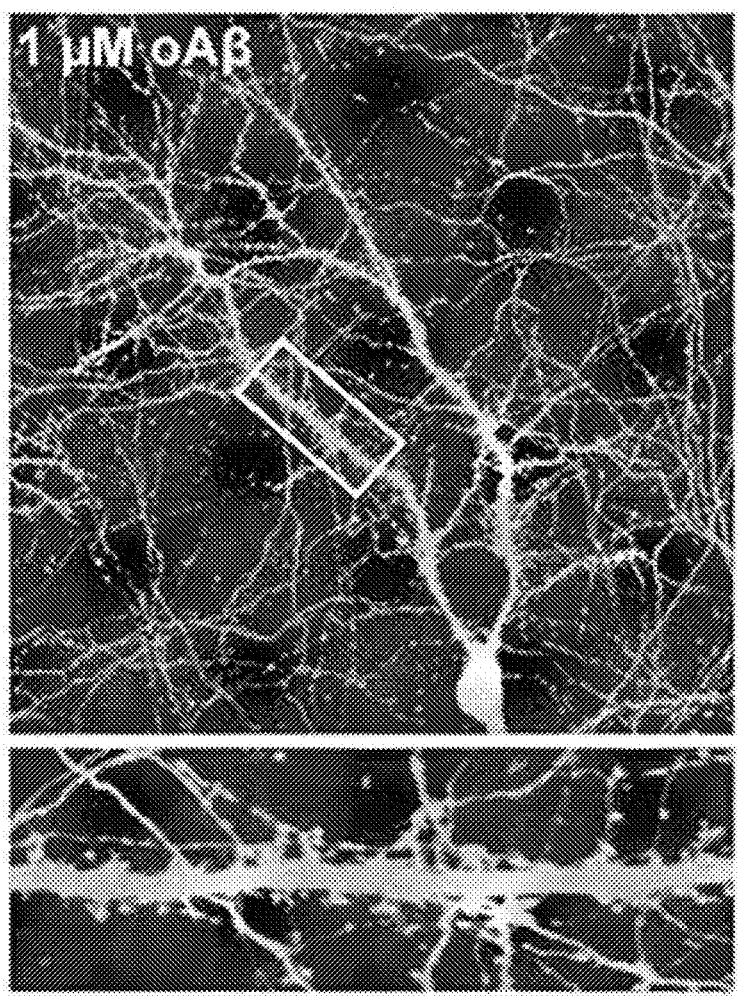
Figure 3C:
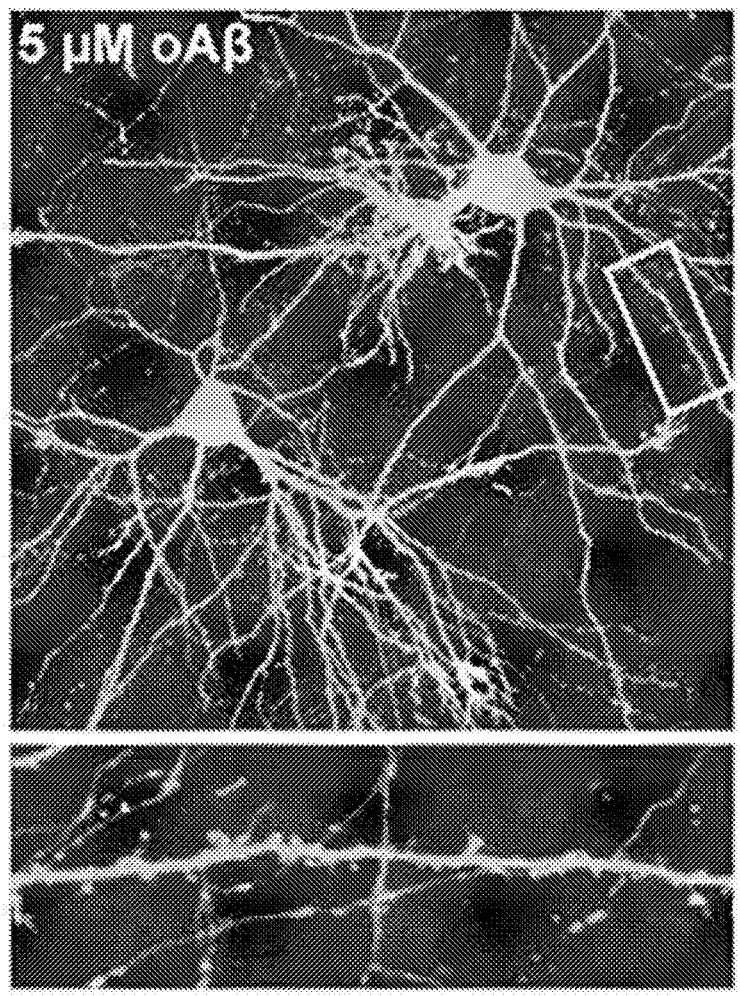
Figure 3D:
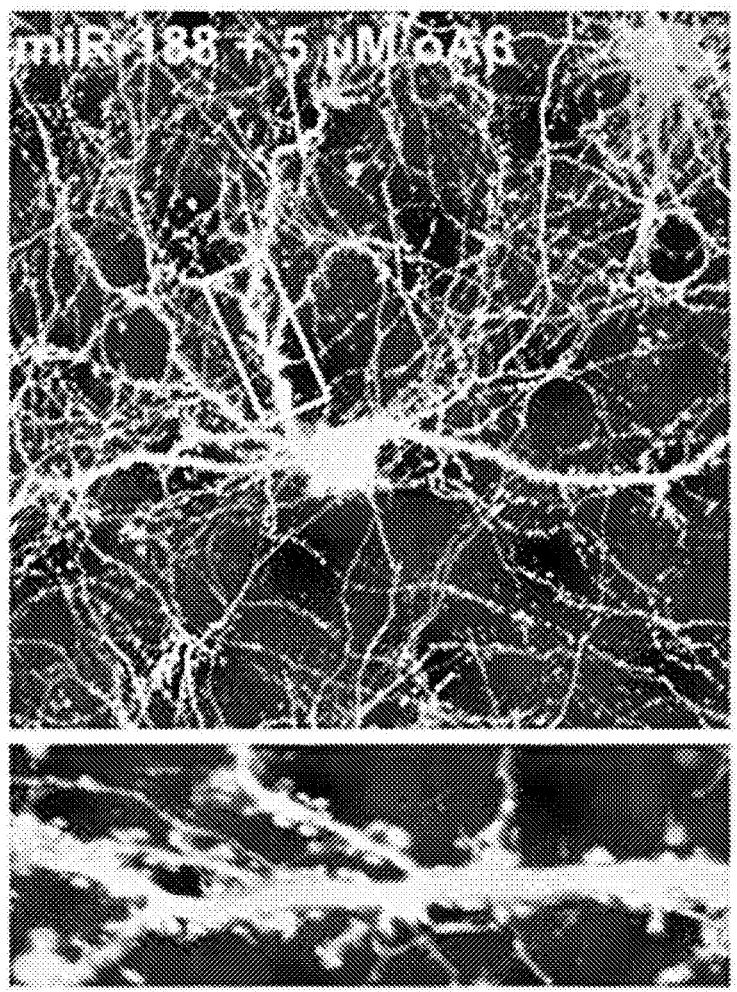
Figure 3E:
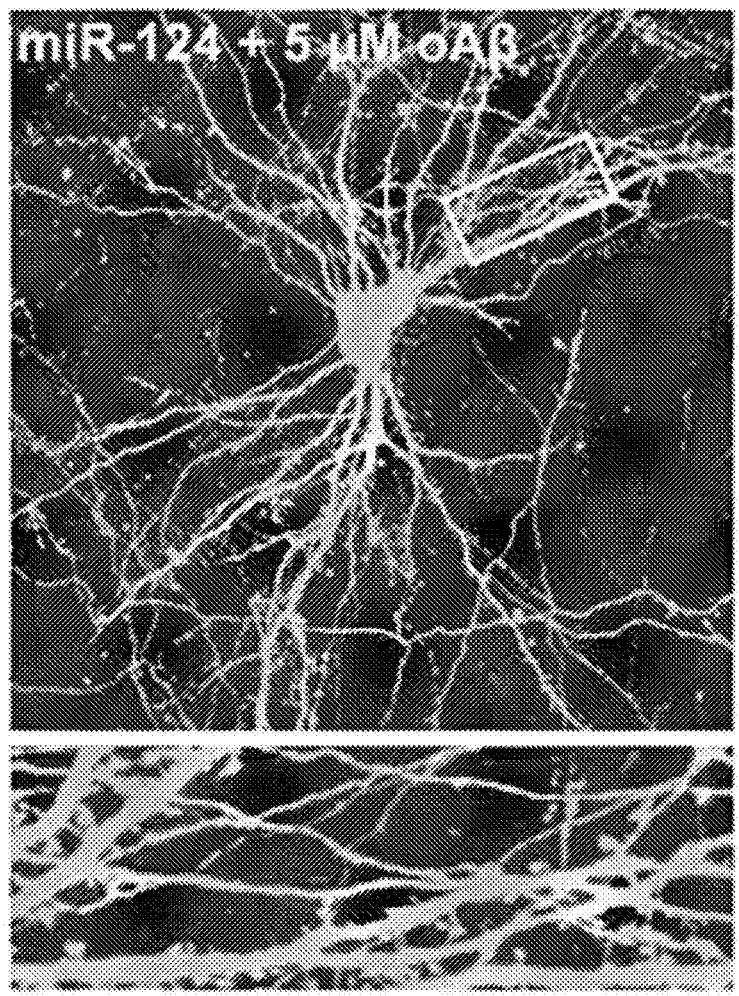
Figure 3F:
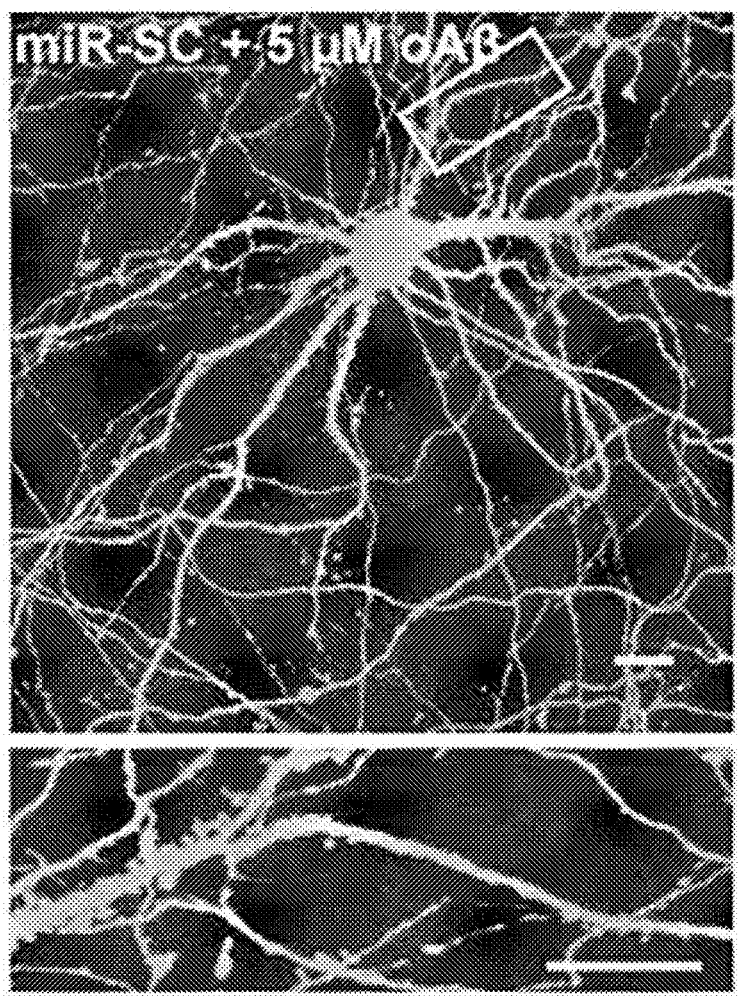
Figure 3G:
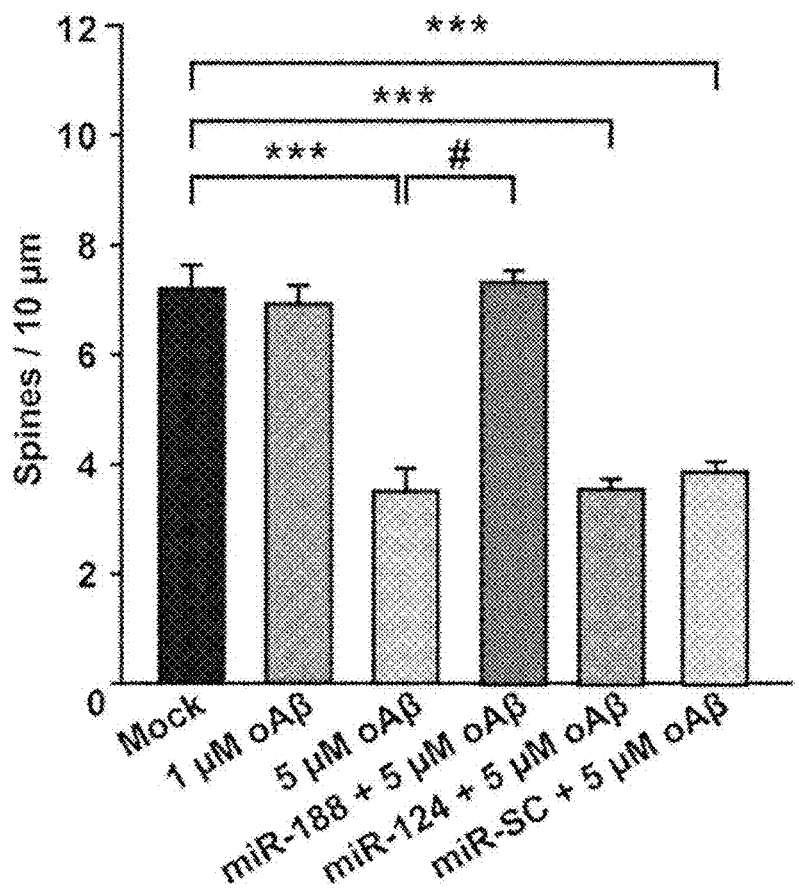
FIG. 3g: Treatment with oAβ (5 μM) for 24 h at DIV 17 induced a significant reduction in dendritic spine density (n=9 neurons, vs. vehicle-treated group, n=10 neurons, one-way ANOVA). However, transfection with the miR-188-5p oligonucleotide rescued the reduction in dendritic spine density induced by treatment with oAβ (n=9 neurons, one-way ANOVA). Data are represented as the mean±SEM. ***p<0.001 compared to Mock; #p<0.01 compared to 5 μM oAb.
Figure 3H:
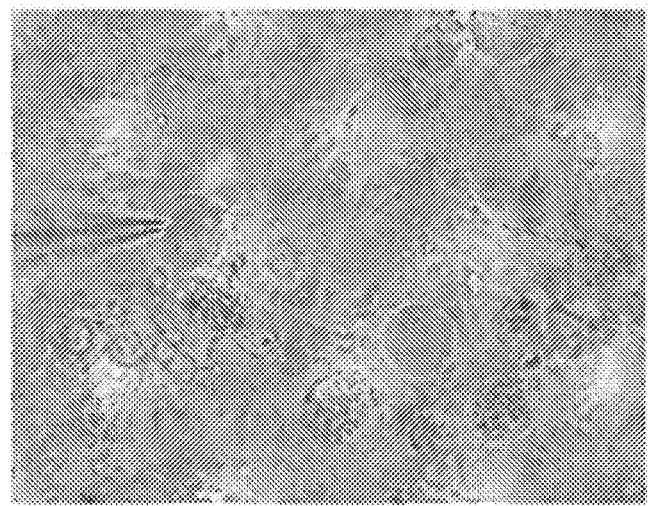
FIG. 3h: Representative images of the single whole-cell recording model used to measure transfected neurons (green arrow) at DIV 18-20.
Figure 3H:
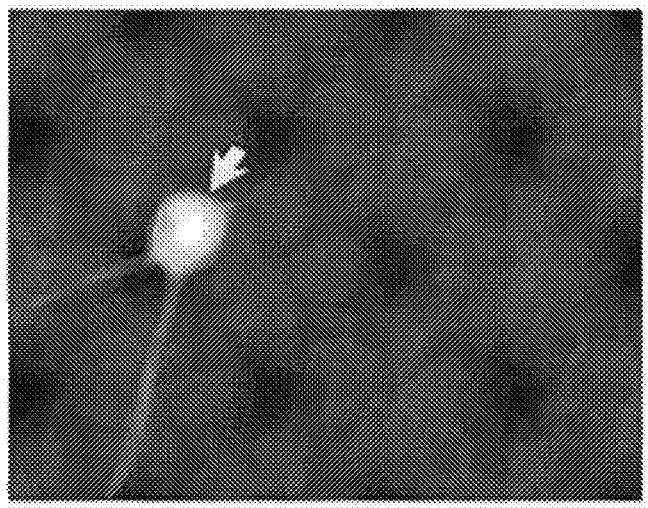
Figure 3I:
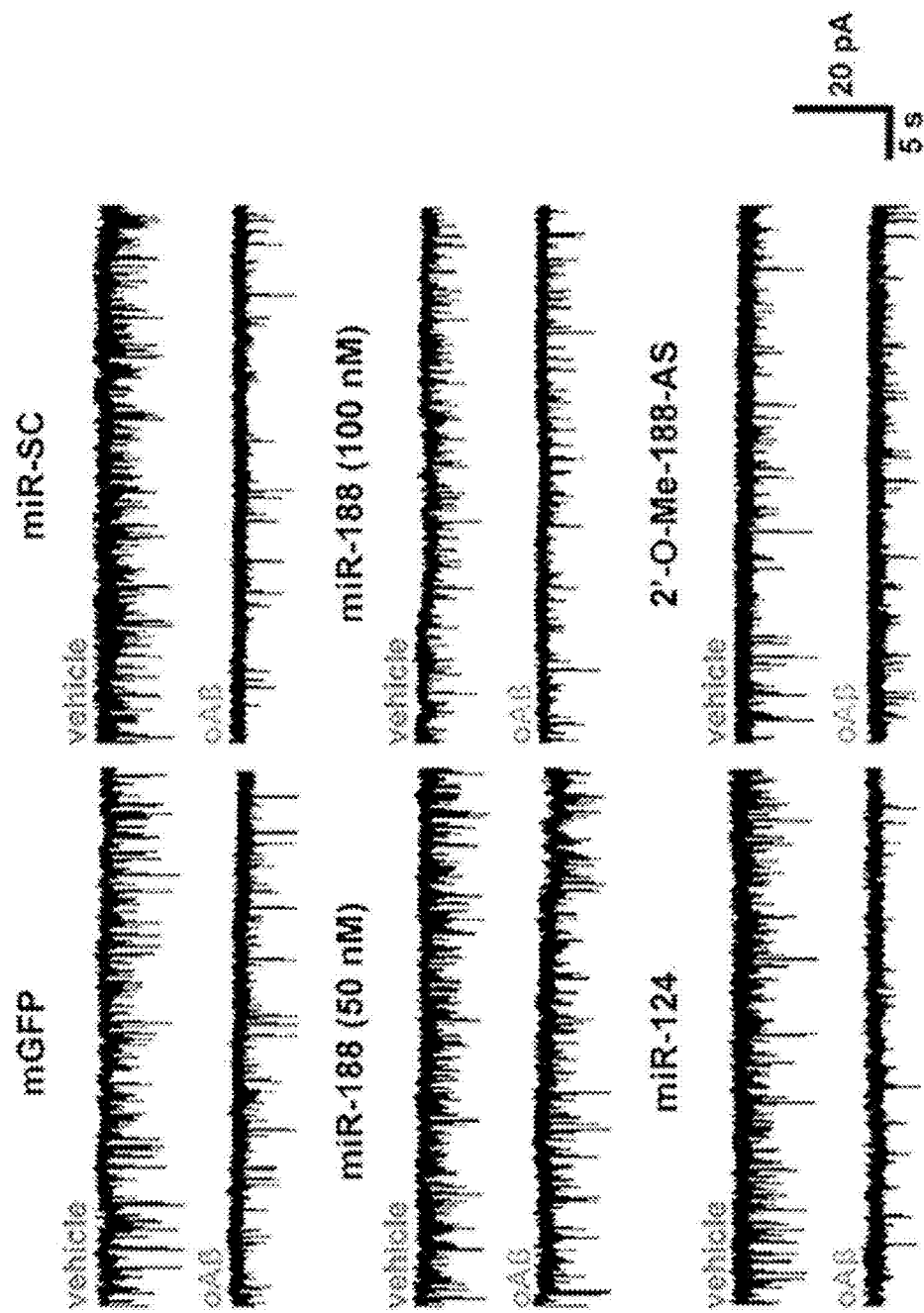
FIG. 3i: Sample traces of mEPSCs recorded in rat primary hippocampal neurons treated with vehicle or 5 μM oAβ either alone or plus transfection with miR-SC, miR-124, miR-188-5p or 2'-O-Me-188-5p-AS oligonucleotides and the IRES-mGFP vector at DIV 10-12. Five minutes of representative mEPSC recordings were used to generate the cumulative distribution plot.
Figure 3J:
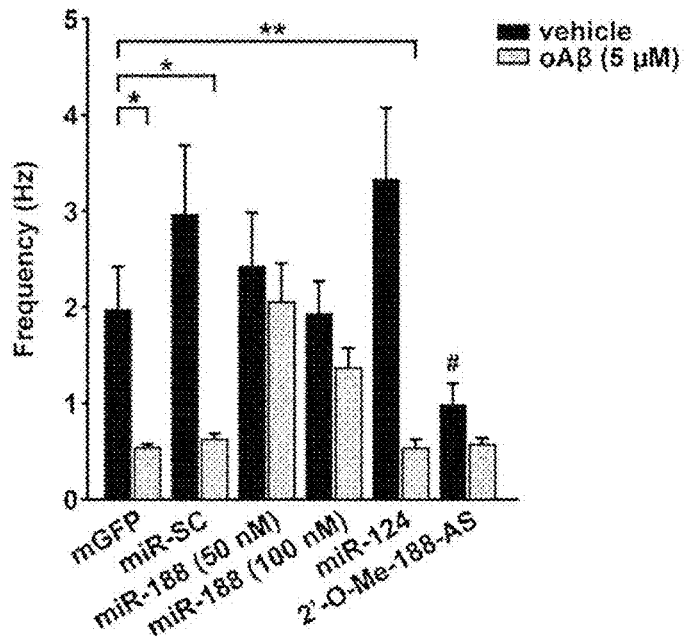
FIG. 3j: Bar graphs show the mean values of mEPSC frequencies of vehicle (black bar) and 5 μM oAβ-treated (gray bar) rat primary hippocampal neurons. Co-transfection of miR-188-5p (50 or 100 nM) with mGFP completely reversed the reduction of mEPSC frequency induced by 5 μM oAβ (n=7 vs. vehicle, n=8, p>0.05). *p<0.05, **p<0.01 compared to mGFP-transfected control.
Figure 3K:
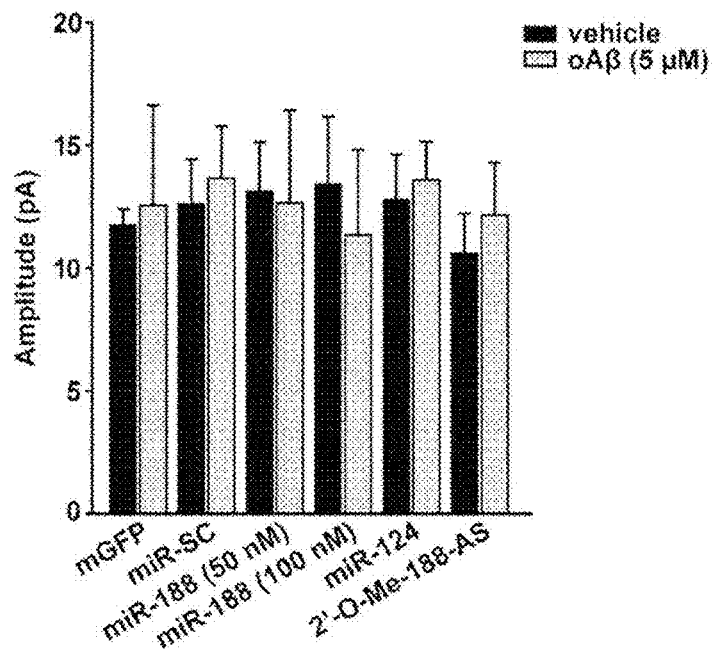
FIG. 3k: The mEPSC amplitudes of rat primary hippocampal neurons treated with each vehicle (black bar) were not altered compared to the 5 μM oAβ-treated neurons (gray bar). The statistical comparisons of synaptic currents were made using the Kolmogorov-Smirnov test. Statistical analysis was performed by an independent T test or nonparametric Mann-Whitney test; data represents the mean±SEM. oAβ=oligomeric Aβ$_{1-42}$.
Figure 3I:
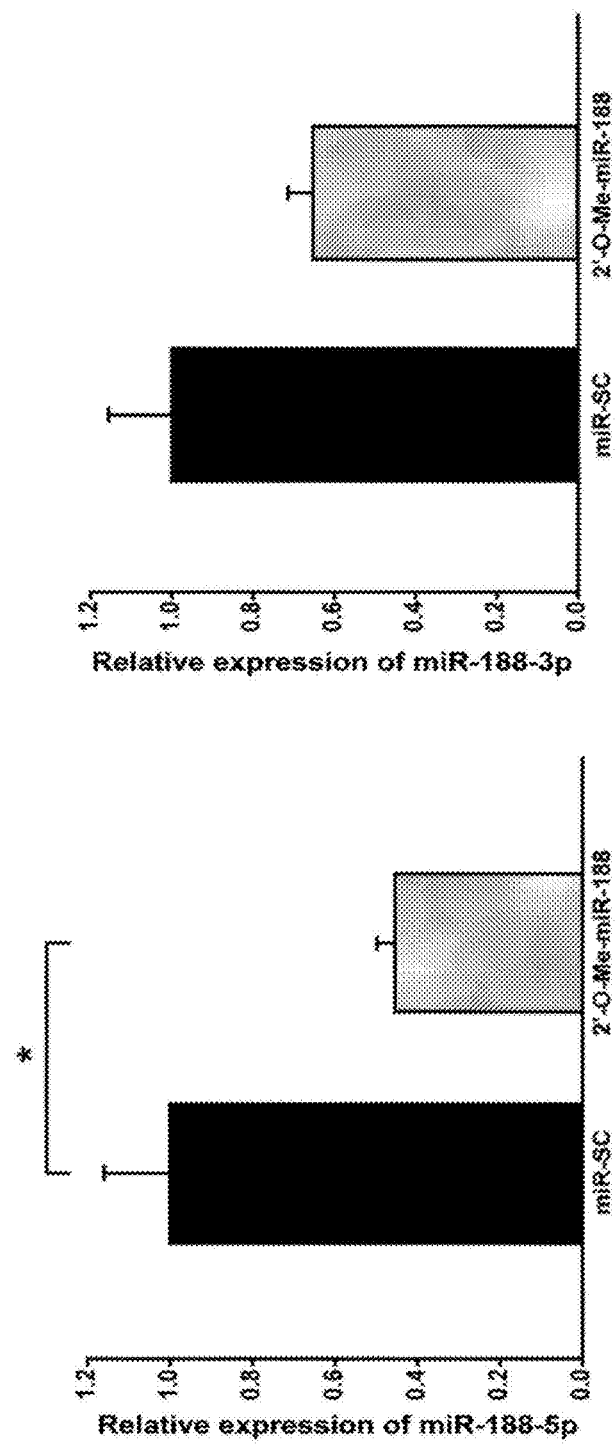

Transfection of rat primary hippocampal neurons with 2'-O-Me-188-5p-AS reduced mEPSC frequency and showed no significant difference when compared to treatment of 2'-O-Me-188-5p-AS treated neurons with $A\beta_{1-42}$ (FIG. 3j). The mEPSC amplitude was similar among any of the groups (FIG. 3k). These results demonstrate that miR-188-5p rescues the reduction in basal synaptic transmission induced by oligomeric A131-42.

Example 4: Restoring of the Synaptic Dysfunction in 5×FAD Mice by miR-188-5p

Figure 4A:
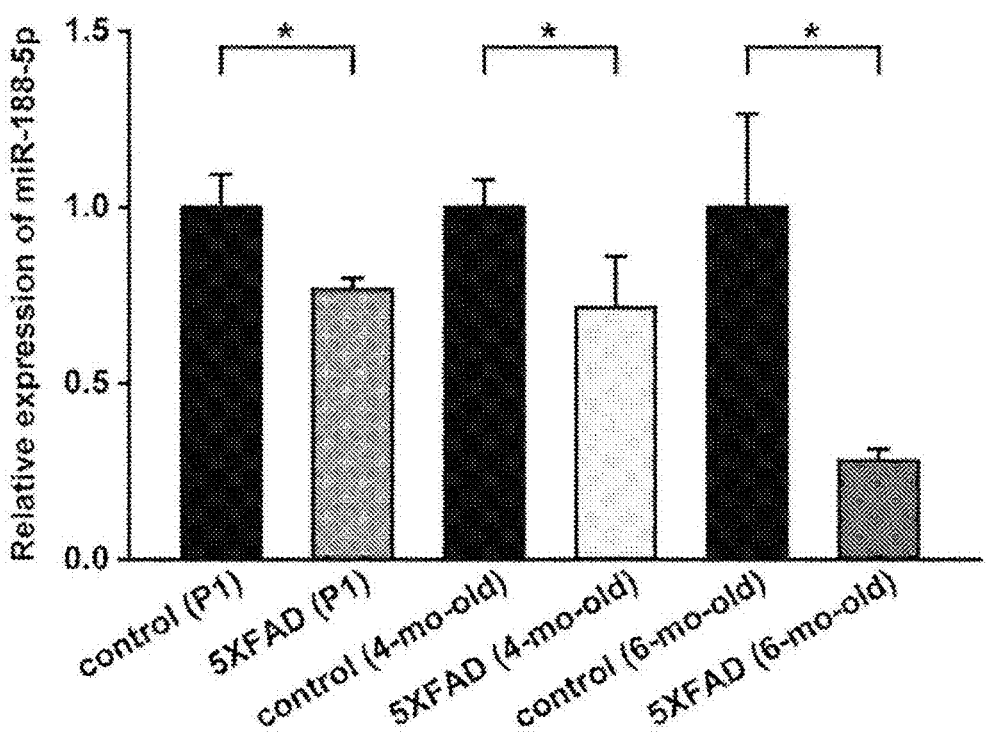
FIG. 4a: miR-188-5p expression in the hippocampus was evaluated with RT-qPCR from P1, 4-month-old and 6-month-old 5×FAD mice. miR-188-5p was significantly down-regulated in the hippocampi of 5×FAD mice (n=11 vs. age-matched controls, n=7; at 4 months of age, n=4 vs. age-matched controls, n=5; at 6 months of age, n=3, vs. age-matched controls, n=4, Student t-test). U6 snoRNA was used as a reference control. The data represent the means±SEM. *p<0.05 compared to age-matched wild-type mice. P1=post-natal day 1.
Figure 4B:
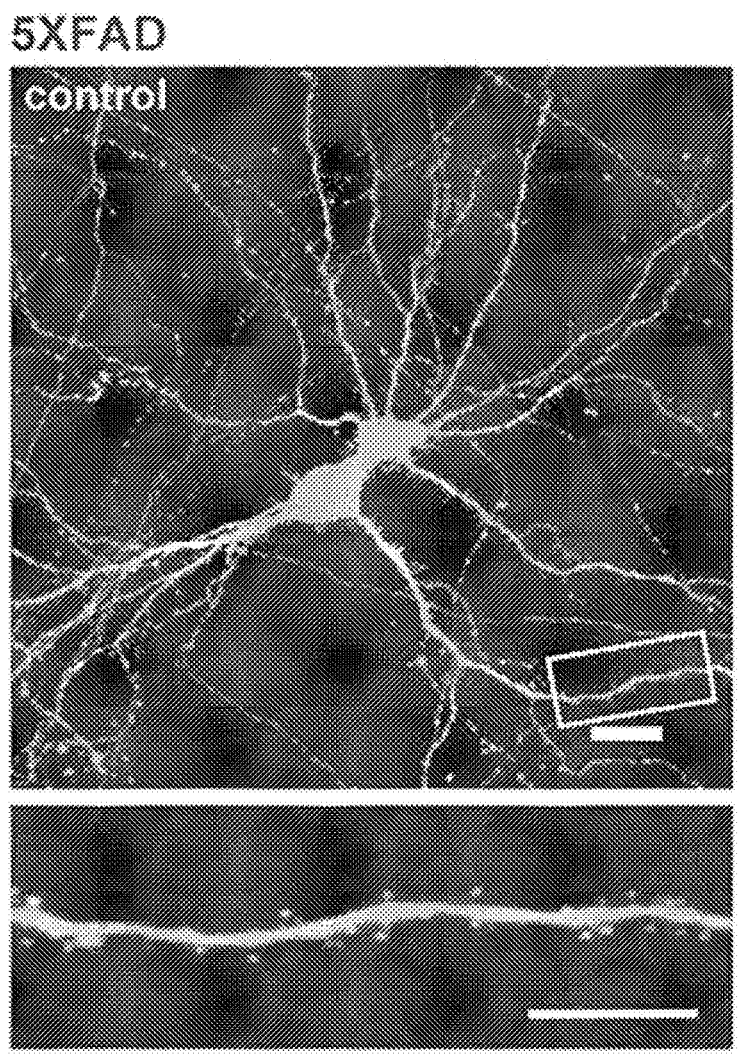
FIGS. 4b, 4c, 4d, 4e, 4f, 4g and 4h: Representative images of dendritic spines in primary hippocampal neurons of P1 wild-type and 5×FAD mice at DIV 18-20. The dendritic segment outlined with a white box (upper) is magnified to delineate the spine morphology (bottom) with a 4× optic zoom. The scale bars indicate 20 and 10 μm in the low- and high-magnification images, respectively.
Figure 4C:
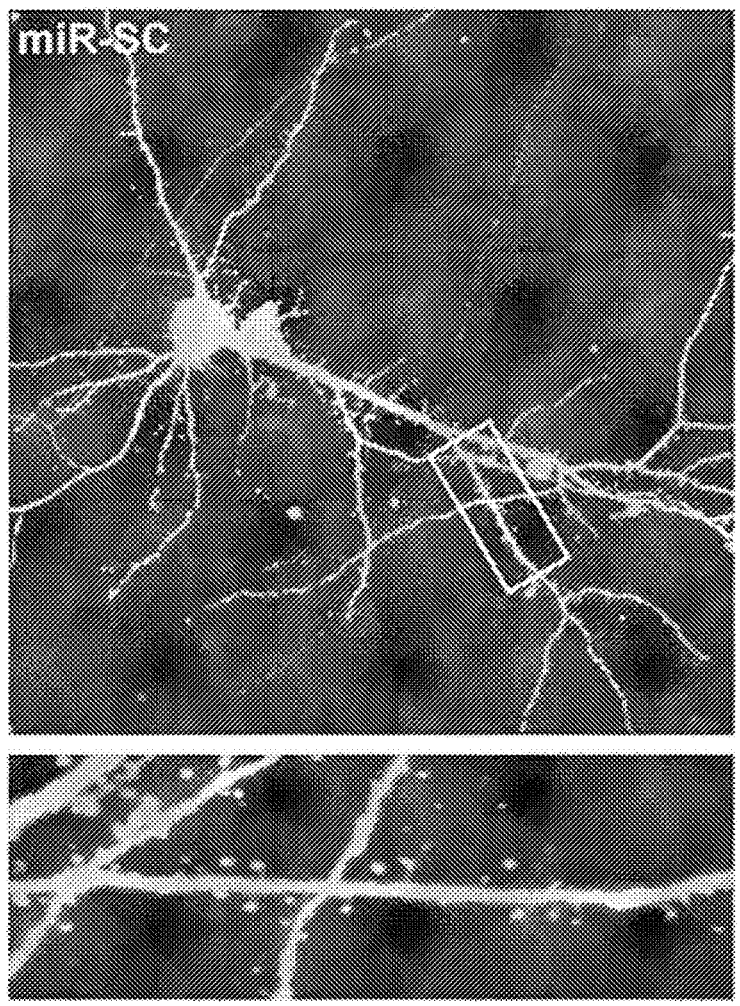

It has been reported that adult 5×FAD mice show synaptic dysfunction in various brain regions34. Whether the expression of miR-188-5p is altered in 5×FAD mice compared with age-matched wild-type mice was observed. RT-qPCR analysis showed that miR-188-5p was significantly down-regulated in the hippocampi of the 5×FAD mice at post-natal day 1 (P1), 4 months of age, and at 6 months of age (at P1, 0.77±0.03, p=0.027; at 4 months of age, 0.72±0.15, p=0.038; at 6 months of age, 0.28±0.03, p=0.014; FIG. 4a). The dendritic spine densities of the primary hippocampal neurons from 5×FAD mice at DIV 18-20 were significantly decreased by 59.74% compared to the neurons from wild-type mice (p<0.001; FIG. 4b,g,i).

Figure 4D:
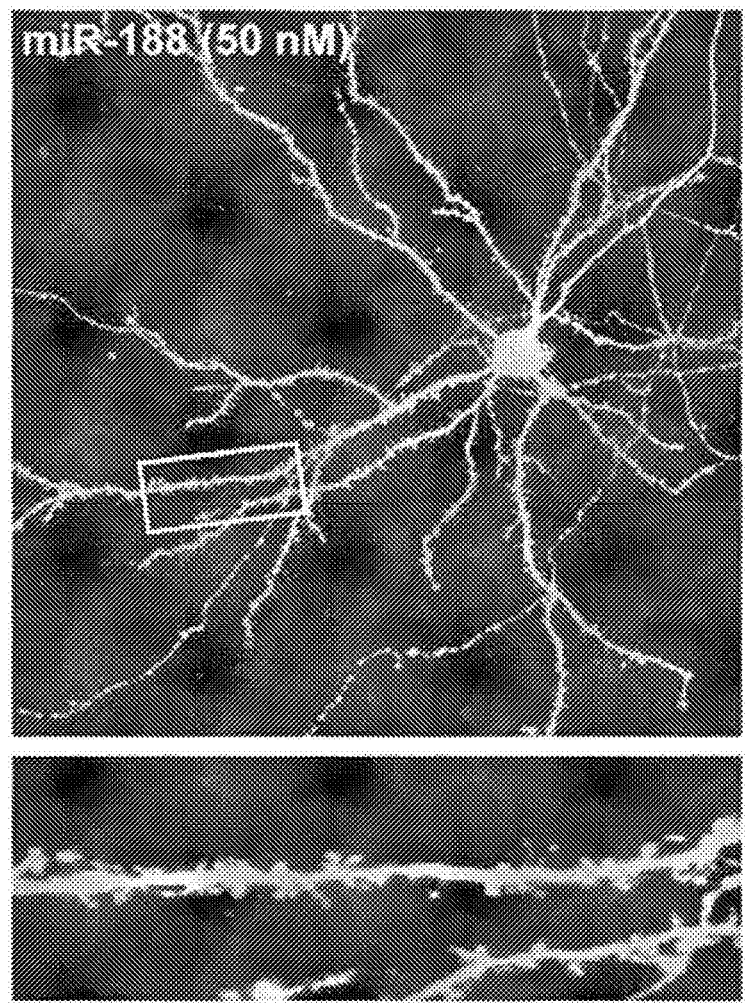
Figure 4E:
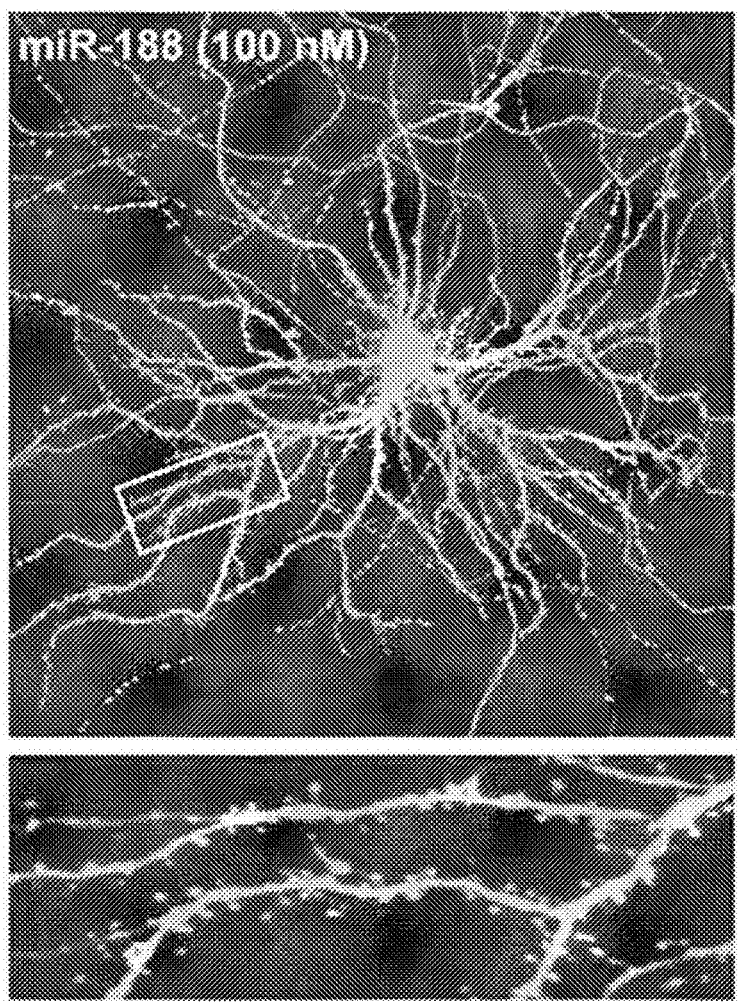
Figure 4F:
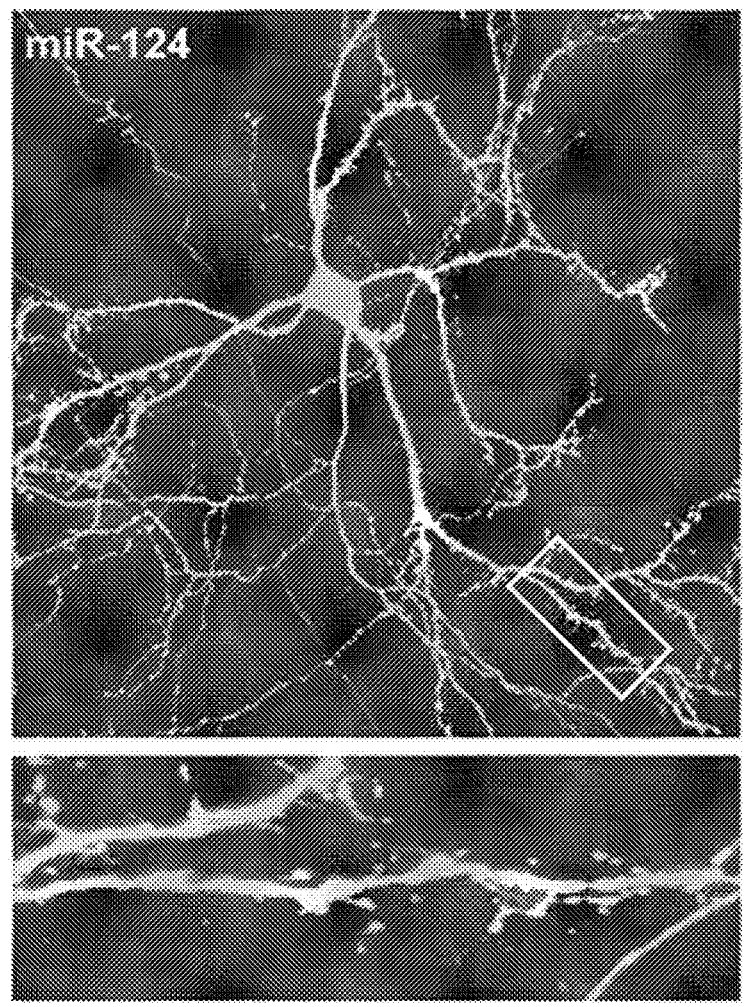
Figure 4G:
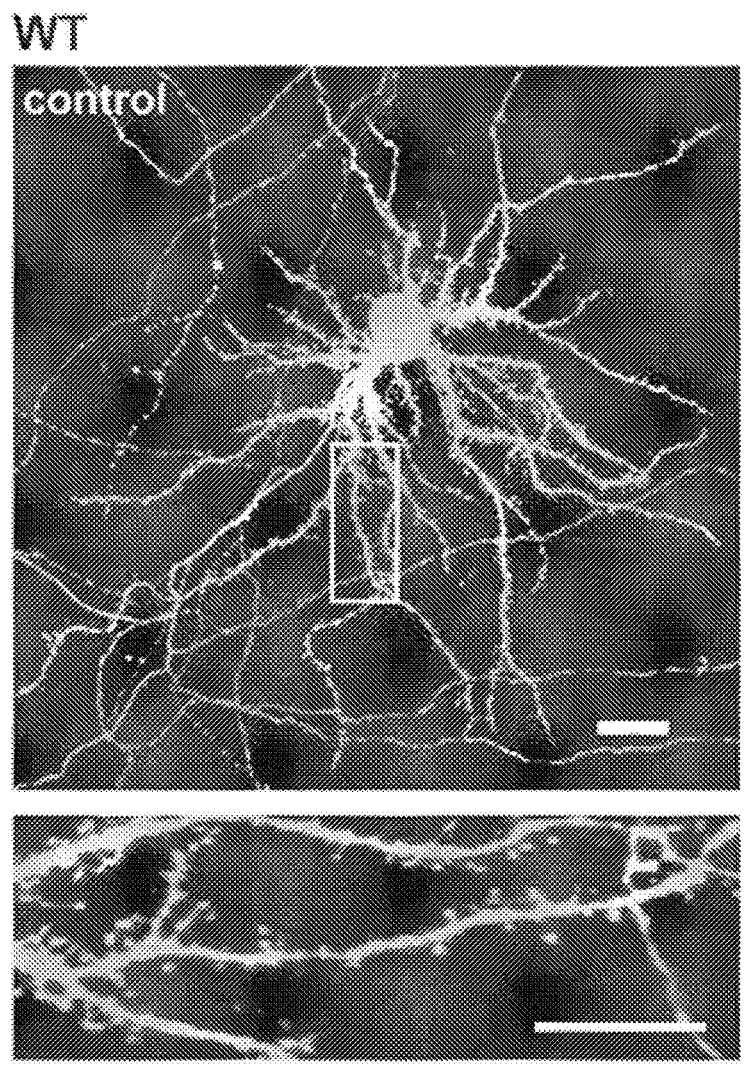
Figure 4H:
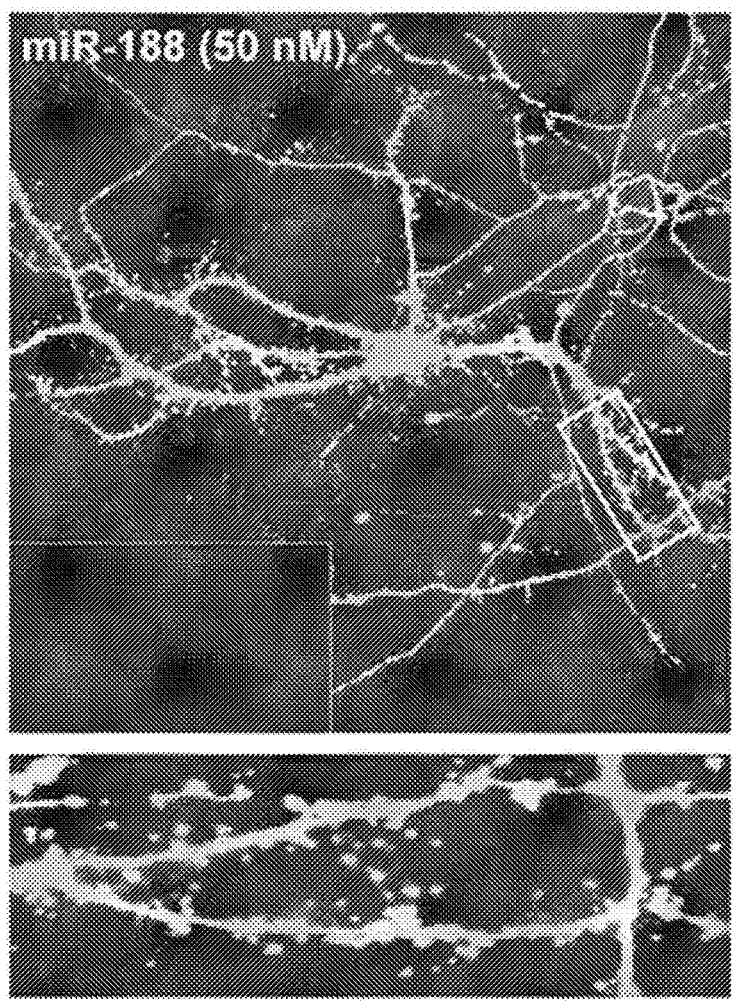
Figure 4I:
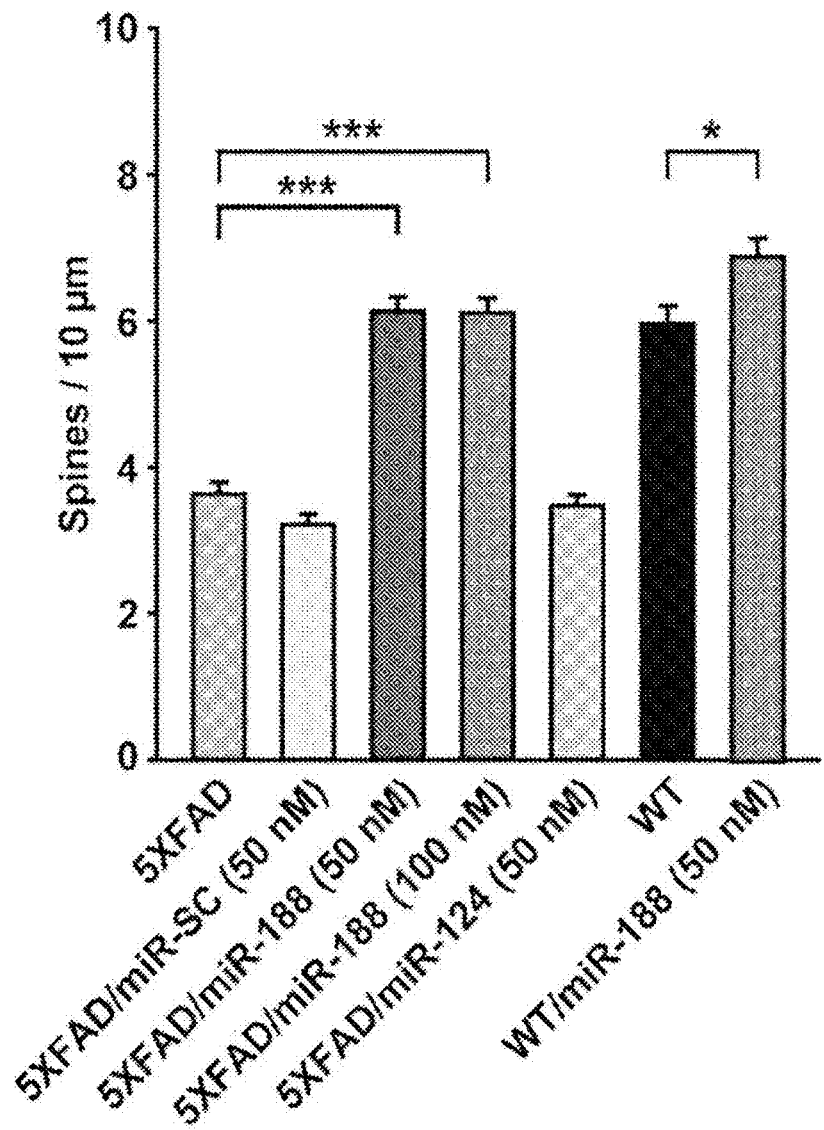
FIG. 4i: A quantification of the spine densities (secondary dendritic spines 50-100 μm from the soma) at DIV 18-20 after transfection into primary hippocampal neurons at DIV 10-12. The dendritic spine densities of neurons from 5×FAD mice at DIV 18-20 were significantly reduced (n=21 neurons, one-way ANOVA) compared to neurons from wild-type mice (n=13 neurons). The addition of miR-188-5p to primary hippocampal neurons from 5×FAD mice significantly rescued the reduction in dendritic spine density in 5×FAD mice (n=22 neurons, one-way ANOVA) compared to the neurons of untreated 5×FAD mice. Data are represented as the mean±SEM. *$p<0.05$, ***$p<0.001$ compared to mGFP-transfected wild-type mice primary hippocampal neurons; #$p<0.001$ compared to mGFP-transfected 5×FAD mice primary hippocampal neurons.

Conversely, the transfection with miR-188-5p oligonucleotide into the neurons significantly rescued the reduction in dendritic spine density in 5×FAD mice compared to only mGFP-transfected neurons from 5×FAD mice (p<0.001; FIG. 4d,e,i). 9-10 neurons were analyzed for each group. The numbers of dendrites analyzed per neuron is 4.52±0.31 (5×FAD), 4.41±0.35 (5×FAD/miR-SC), 4.24±0.34 (5×FAD/miR-188 50 nM), 3.75±0.27 (5×FAD/miR-188 100 nM), 4.00±0.36 (5×FAD/miR-124), 5.46±0.62 (wild-type) or 3.29±0.29 (wild-type/miR-188 50 nM).

It was shown that primary hippocampal neurons from 5×FAD mice exhibited a reduction in dendritic spine density compared to neurons from wild-type mice. A previous report demonstrated that neurons prepared from Tg2576 mice exhibited abnormal morphologies and lower spine density compared to neurons from wild-type control animals. This result is because the higher level of Aβ is formed in neuron culture as shown in the previous paper36. Moreover, we confirmed that this was a miR-188-5p-specific effect as no significant rescue was observed after transfection with either miR-SC or miR-124 (IG. 4b,c,f,i).

Example 5: Restoring of the Memory Deficits in 5×FAD Mice by miR-188-5p

Figure 5A:
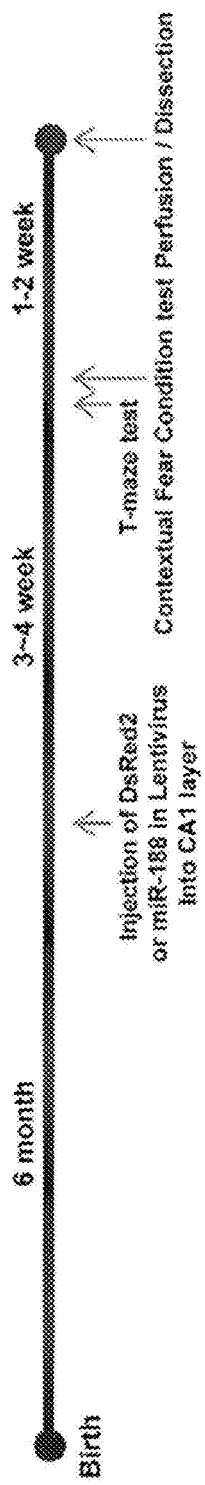
FIG. 5a: Experimental schedule for miR-188-5p overexpression in wild-type and 5×FAD mice. Mice were trained with 3 foot shocks (0.7 mA, 2 sec) for contextual fear conditioning.
Figure 5B:
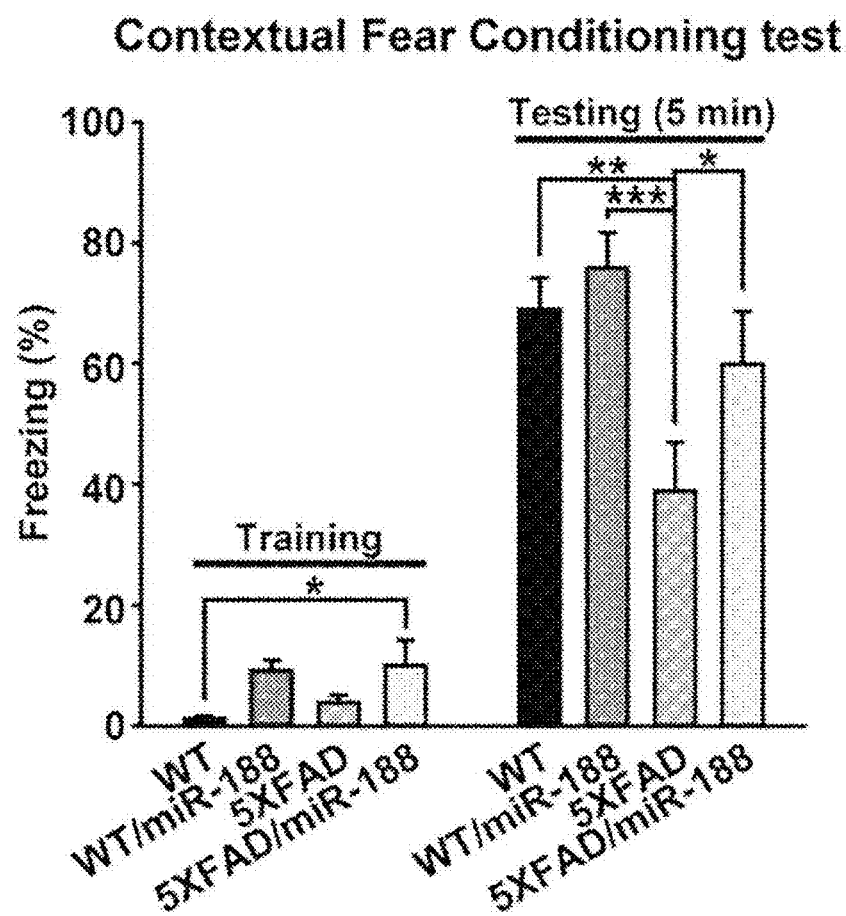
FIG. 5b: 5×FAD mice showed significantly lower levels of contextual freezing than wild-type mice when tested 1 day after training. 5×FAD/miR-188-5p mice showed complete rescue of freezing, similar to the wild-type mice (n=8-10 mice per group, one-way ANOVA).
Figure 5C:
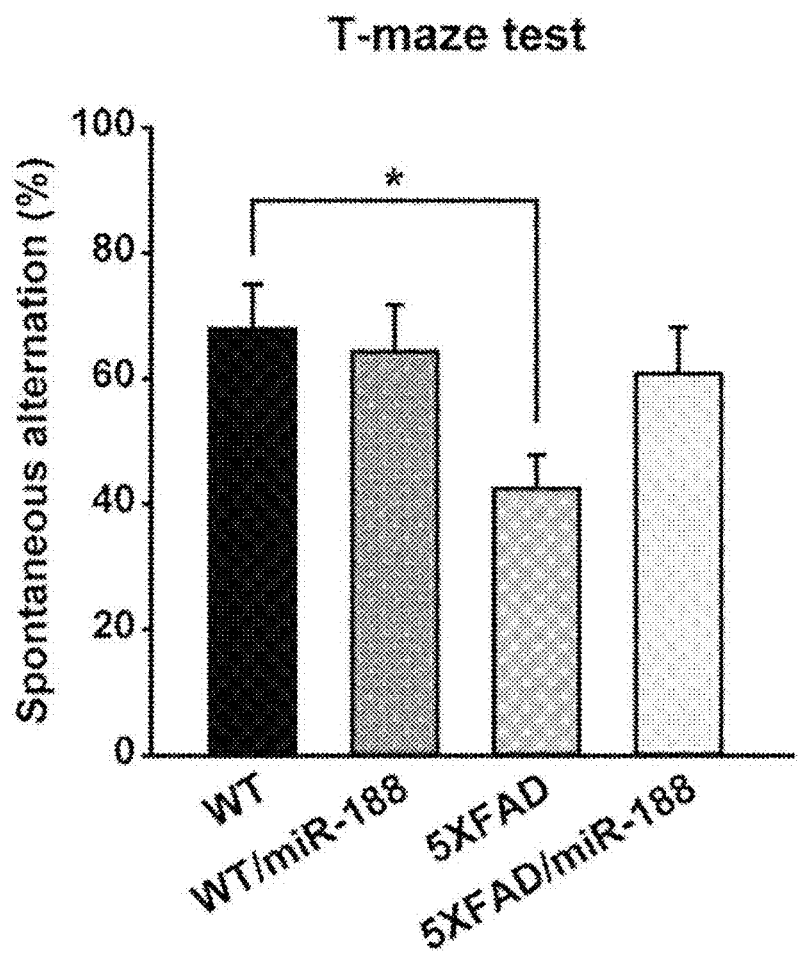
FIG. 5c: 5×FAD mice showed significantly reduced levels of spontaneous alternation performance in the T-maze (n=14, one-way ANOVA), compared to wild-type mice (n=10). Viral-mediated expression of miR-188-5p restored the reduction in spontaneous alternation performance shown in 7-month-old 5×FAD mice (n=11, one-way ANOVA). *$p<0.05$, $p<0.01$ and *$p<0.001$ compared to control virus injected 5×FAD mice; #$p<0.05$ compared to control virus injected wild-type mice.
Figure 5D:
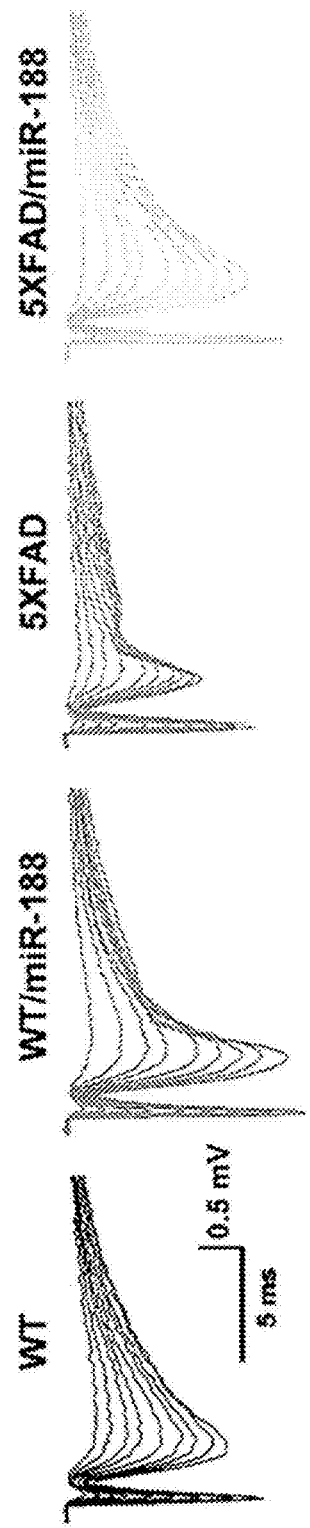
FIGS. 5d, 5e and 5f: Restoration of basal synaptic transmission in 5×FAD mice by miR-188-5p expression.
Figure 5E:
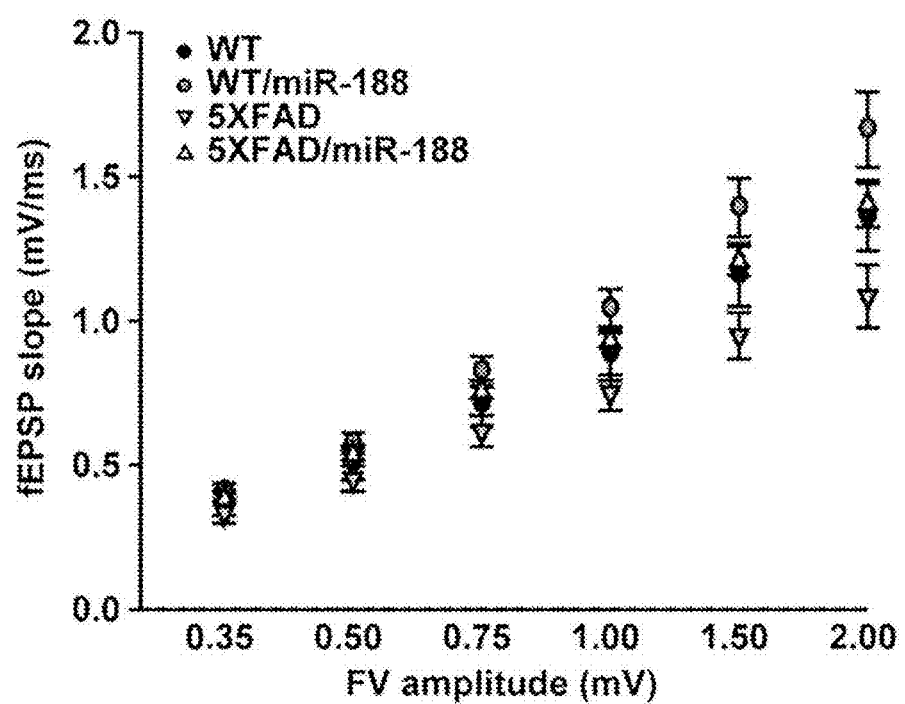
Figure 5F:
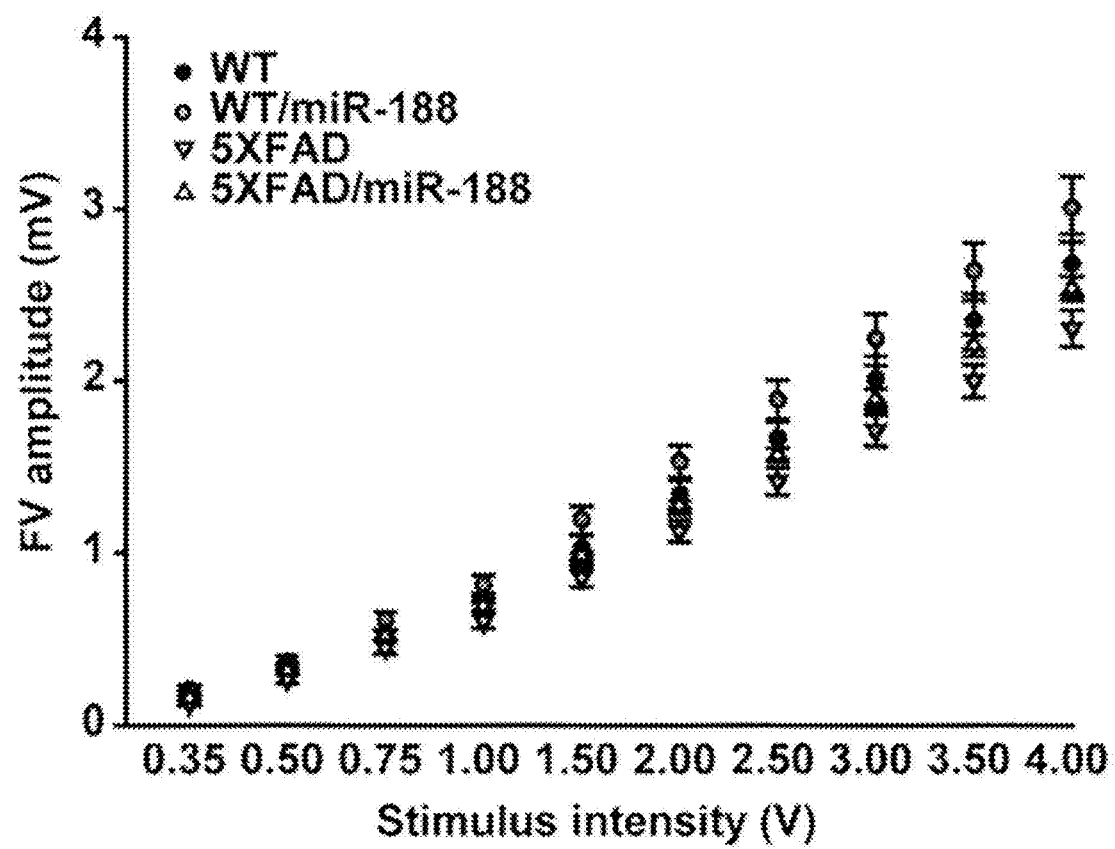
Figure 5G:
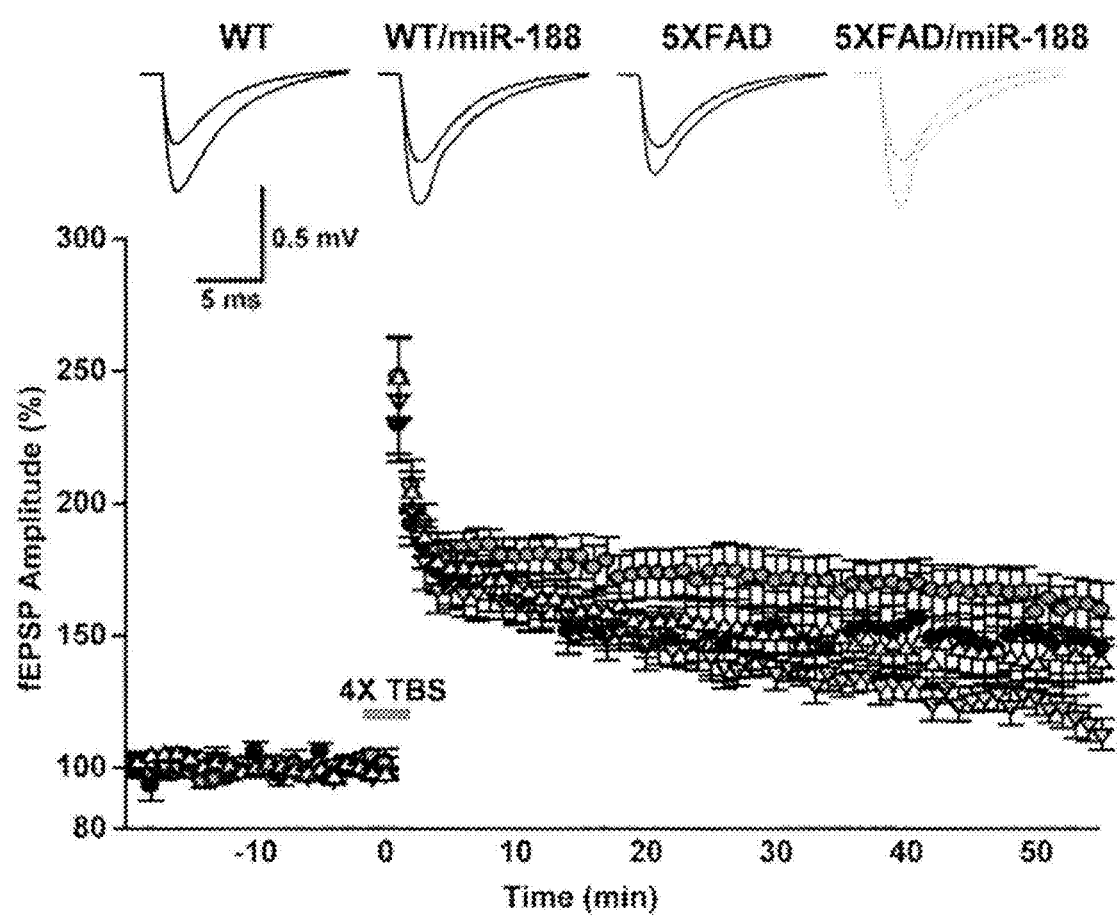
FIGS. 5g and 5h: Impaired LTP in 5×FAD mice was recovered by miR-188-5p expression.
Figure 5H:
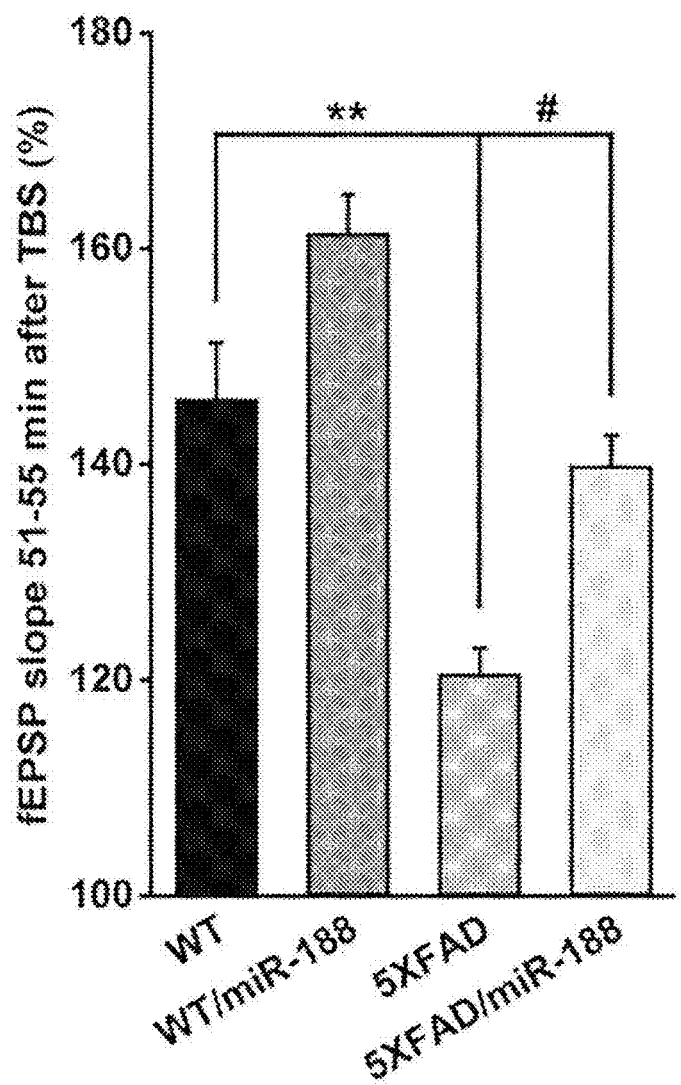
Figure 5I:
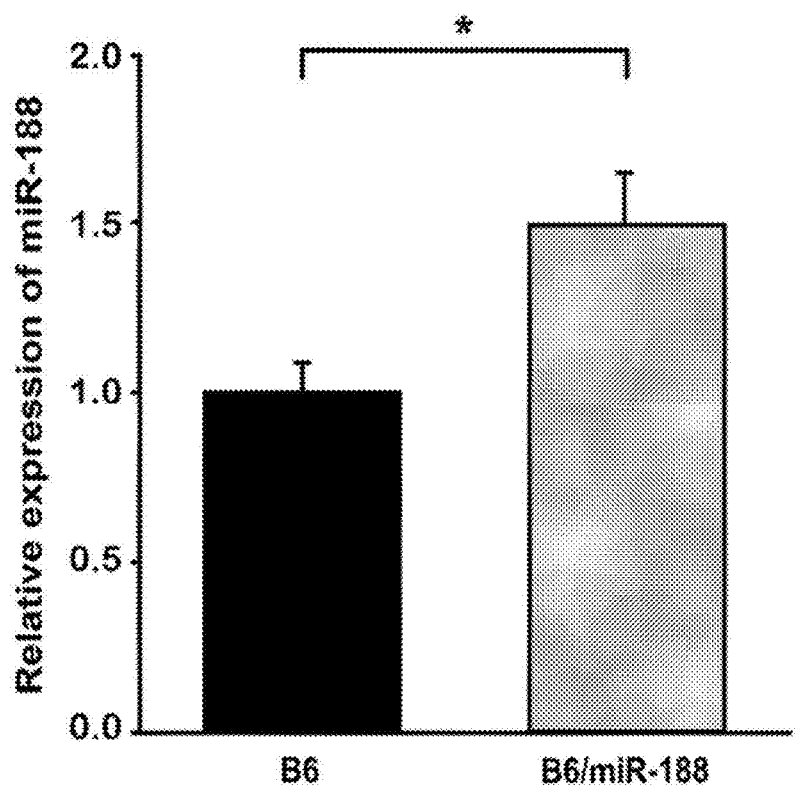
FIG. 5i: The result confirming the expression of miR-188-5p in hippocampi of naïve mouse in 3 weeks after stereotaxic injection of the vector in which miR-188-5p is subcloned.

To further explore whether the reduction in miR-188-5p expression observed in the brains from AD patients and 5×FAD mice regulates cognitive function due to changes in synaptic structure and basal synaptic function, miR-188-5p subcloned in a lentiviral vector in the CA1 region was expressed (FIG. 5a) and miR-188-5p expression in the hippocampus of naive mice 3 weeks after stereotaxic injection was confirmed (FIG. 5i).

A schematic diagram of the experimental procedure is shown in FIG. 5a. To examine if miR-188-5p expression ameliorates the deficits in hippocampus-dependent learning and memory observed in 7-month-old 5×FAD mice, we first performed a contextual fear conditioning test, in which mice learn to associate a distinct context with aversive footshocks. Wild-type mice exhibited a robust conditional fear response, which was assessed by freezing when returned to the conditioning chamber after training. 5×FAD mice (38.48±8.04%, p=0.004) exhibited a strongly lower percentage of freezing compared with wild-type controls (68.27±5.23%). However, viral-mediated expression of miR-188-5p in 5×FAD mice significantly rescued freezing behavior. These mice showed higher levels of freezing (59.33±8.67%, p=0.047), similar to wild-type controls (FIG. 5b).

Next, spatial working memory in 5×FAD mice was measured using T-maze. These mice showed significantly reduced levels of spontaneous alternation performance (37.50±5.10, p=0.002), compared to wild-type mice (67.50±5.34; FIG. 5c). Expression of miR-188-5p reversed the reduction in spontaneous alternation performance (56.82±7.61, p=0.037).

To investigate the synaptic mechanisms underlying the enhancement of learning and memory by miR-188-5p, first, basal synaptic transmission at the Schaffer collateral (SC)-CA1 synapses through fEPSP recording was examined. Consistent with previous observations, 5×FAD mice showed clear synaptic deficits (FIG. 5d). The relationship between the fEPSP slope and the fiber volley (FV) amplitude was significantly reduced in 5×FAD mice compared with wild-type control mice (FIG. 5e). However, FV amplitude stimulation intensity ratios were not different in all experimental groups (FIG. 5f). These results imply that reduced synaptic transmission in 5×FAD mice might stem from deleterious effects of Aβ on postsynaptic compartments rather than a reduced number of active presynaptic fiber. Unexpectedly, viral-mediated expression of miR-188-5p in the 5×FAD CA1 neurons significantly increased synaptic strength. The fEPSP slope to FV amplitude ratios of 5×FAD/miR-188-5p mice were almost indistinguishable from those of control mice.

Next, the effect of miR-188-5p expression on synaptic LTP was examined. Although repeated trains of theta-burst stimulation (4×TBS) induced synaptic potentiation at SC-CA1 synapses in all experimental groups (FIG. 5g), genotype-specific differences in magnitude and duration of potentiation could be observed. This observation is consistent with several previous studies. While control slices exhibited stable enhancement of synaptic transmission (147.02±5.48% at 50 min after 4×TBS), LTP in 5×FAD slices gradually decreased in magnitude toward baseline during the recording (121.5895±2.4389% at 50 min after 4×TBS, p<0.01). Notably however, impaired LTP in 5×FAD mice almost completely recovered to a normal magnitude with miR-188-5p replenishment in CA1 neurons and no significant difference in LTP was detected between 5×FAD/miR-188-5p and wild-type mice (141.50±2.93% at 50 min after 4× TBS; FIG. 5g,h). These results suggest that miR-188-5p replenishment rescues synaptic dysfunction in 5×FAD mice, and that dysregulation of an activity-regulated miR-188-5p might be associated with memory deficits in 5×FAD mice.

Example 6: Regulation of miR-188 Expression by CREB

The regulatory mechanism for miR-188 expression was researched. First, whether LTP induction increases transcription levels of miR-188 was tested. It was shown that levels of miR-188 primary transcript (pri-miR-188) were significantly increased in rat hippocampal slices by chemical LTP induction, suggesting that miR-188 levels are likely up-regulated at the transcriptional level. Then, transcription factors critical for LTP-mediated upregulation of miR-188-5p were identified.

Figure 6A:
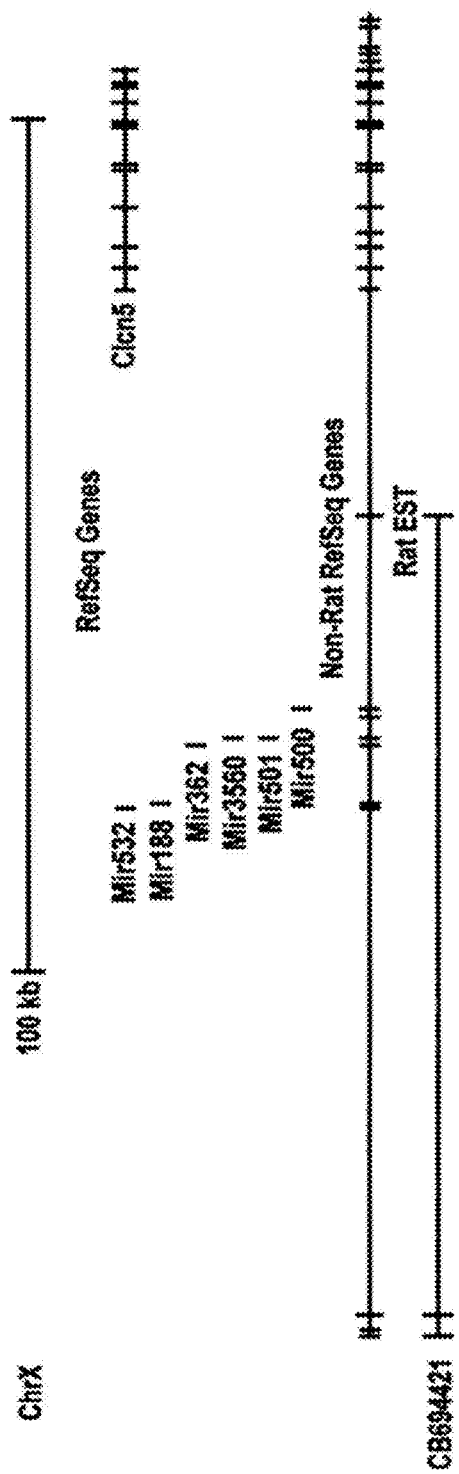
FIG. 6a: The location of miR-188, CB694421, and Clcn5 is shown using the USCS genome browser.

For this, the genomic locations of MIR188 gene in the rat genome via the UCSC genome browser was determined, and it was found that MIR188 gene is located at approximately 50 kb upstream from the transcriptional start site of the Clcn5 gene on the X-chromosome (FIG. 6a). Also, it was found that there was an expressed sequence tag (EST) containing MIR188 gene (CB694421), suggesting that CB694421 might serve as pri-miR-188.

Figure 6B:
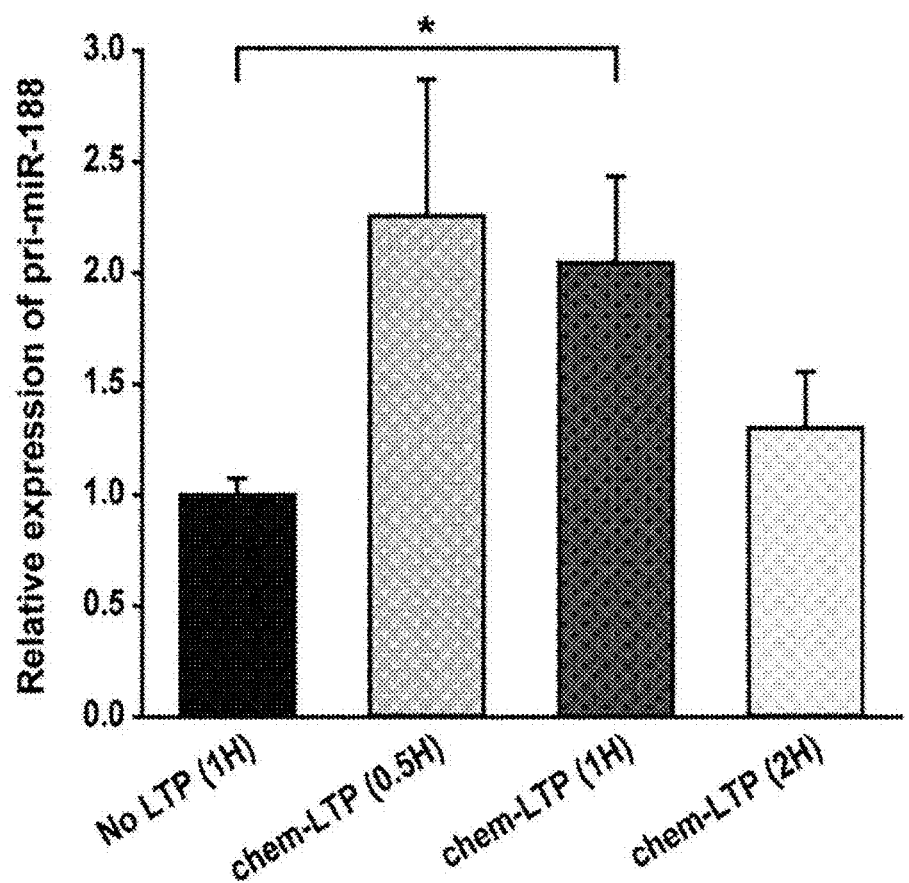
FIG. 6b: RT-qPCR was performed to investigate the changes in pri-miR-188 by chemical LTP induction. Pri-miR-188 level was significantly increased in rat hippocampal slices by chemical LTP induction (No; n=3, 0.5 h; n=3, 1 h; n=3, 2 h; n=3, one-way ANOVA). *$p<0.05$ compared to No LTP. Pri-miR-188 level was significantly increased in rat hippocampal slices by chemical LTP induction (No; n=3, 0.5 h; n=3, 1 h; n=3, 2 h; n=3, one-way ANOVA). *$p<0.05$ compared to No LTP.

Given this finding, analysis on transcription factor binding sites in the promoter region of CB694421 using TRANS-FAC was performed. One CREB binding site within 2 kb upstream from the 5'end of CB694421 was found. The chemical induction of LTP increased the level of pri-miR-188 in the rat hippocampal slices (204.59±38.87%, p=0.034; FIG. 6b).

Figure 6C:
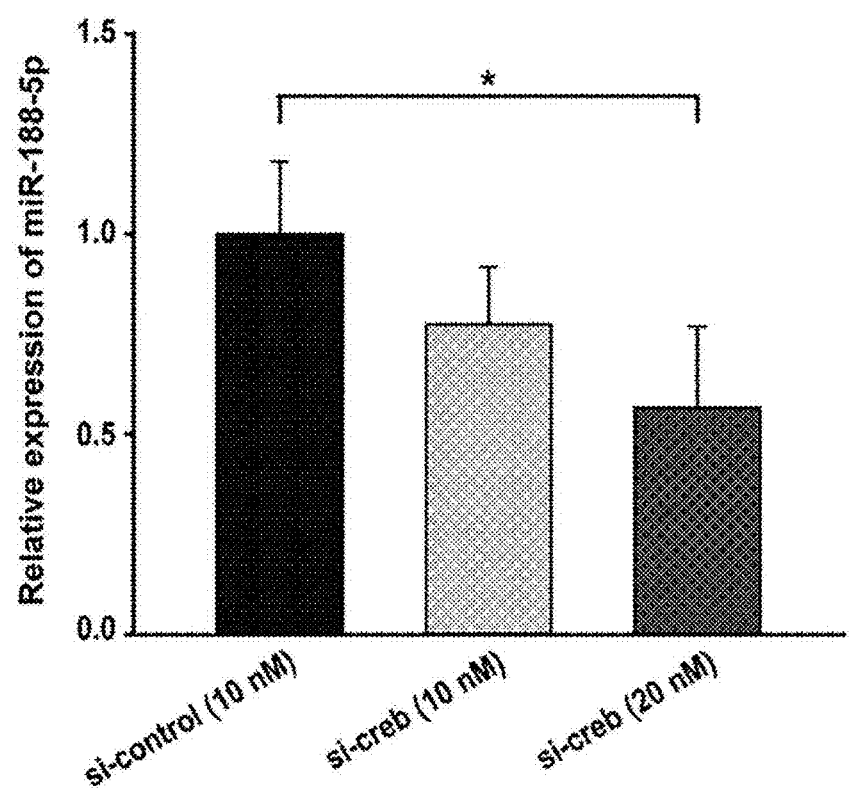
FIG. 6c: RT-qPCR was performed to investigate the changes in miR-188-5p followed by Creb knockdown. Knockdown of Creb using Creb siRNAs resulted in significant downregulation of mature miR-188-5p levels in rat primary hippocampal neurons (si-creb 10 nM; n=4, si-creb 20 nM; n=4, compared to control; n=3, oneway ANOVA). *$p<0.05$ compared to control siRNAs.
Figure 6D:
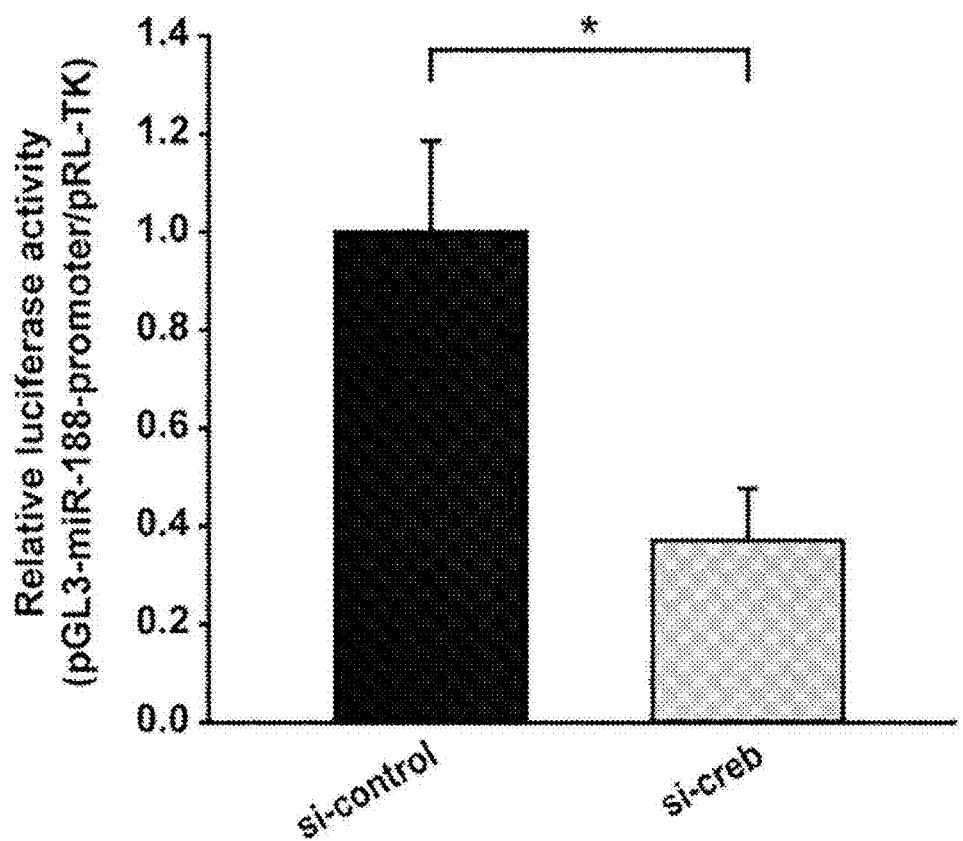
FIG. 6d: miR-188 promoter activity was significantly reduced by Creb knockdown. (n=3, compared to control siRNAs, Student's t-test) in rat primary hippocampal neuron cultures. *$p<0.05$ compared to control siRNAs.
Figure 7:
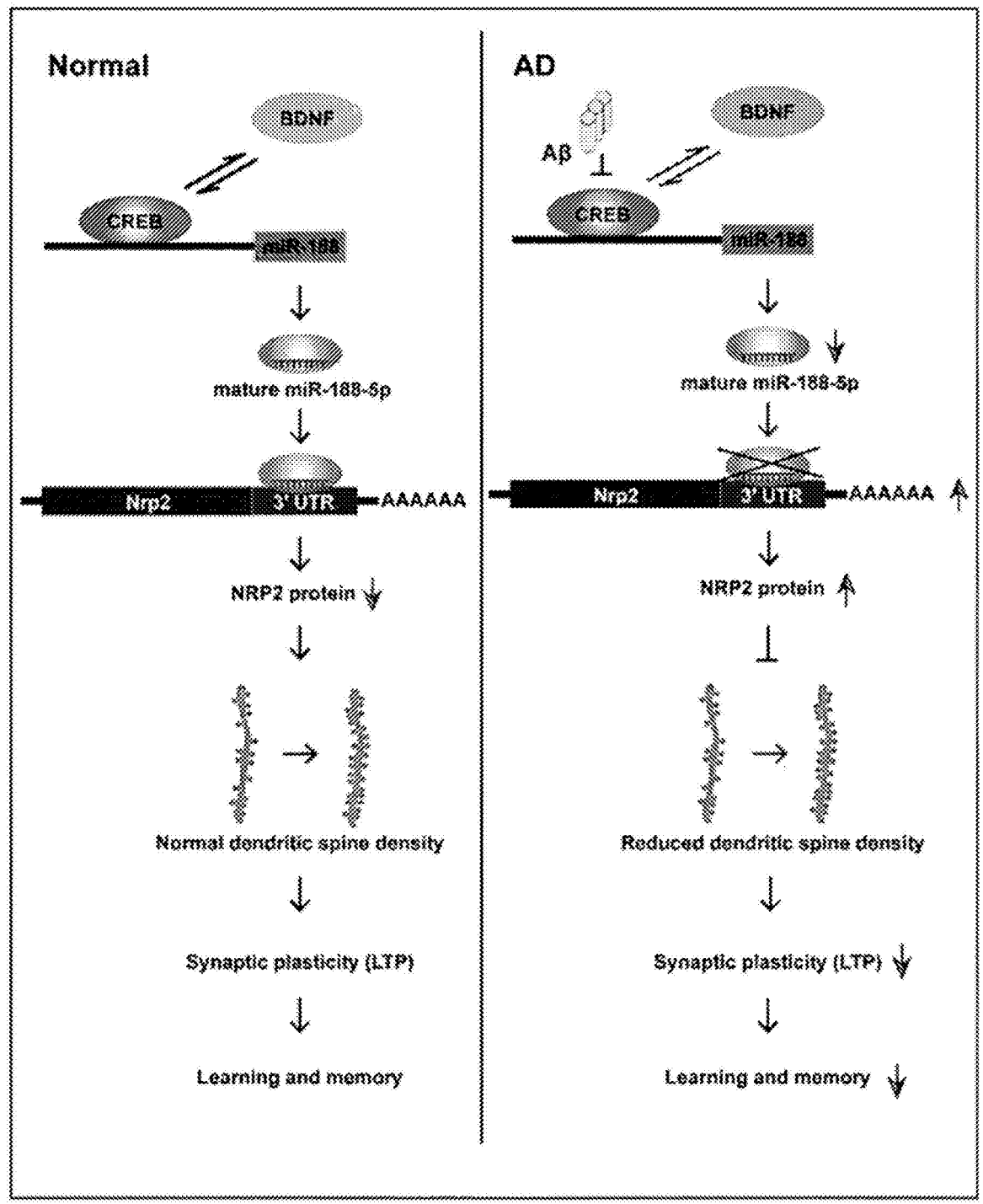
FIG. 7 is a schematic diagram showing the possible relationship between miR-188-5p, Nrp-2, BDNF and CREB in steady-state and AD conditions.
Figure 8:
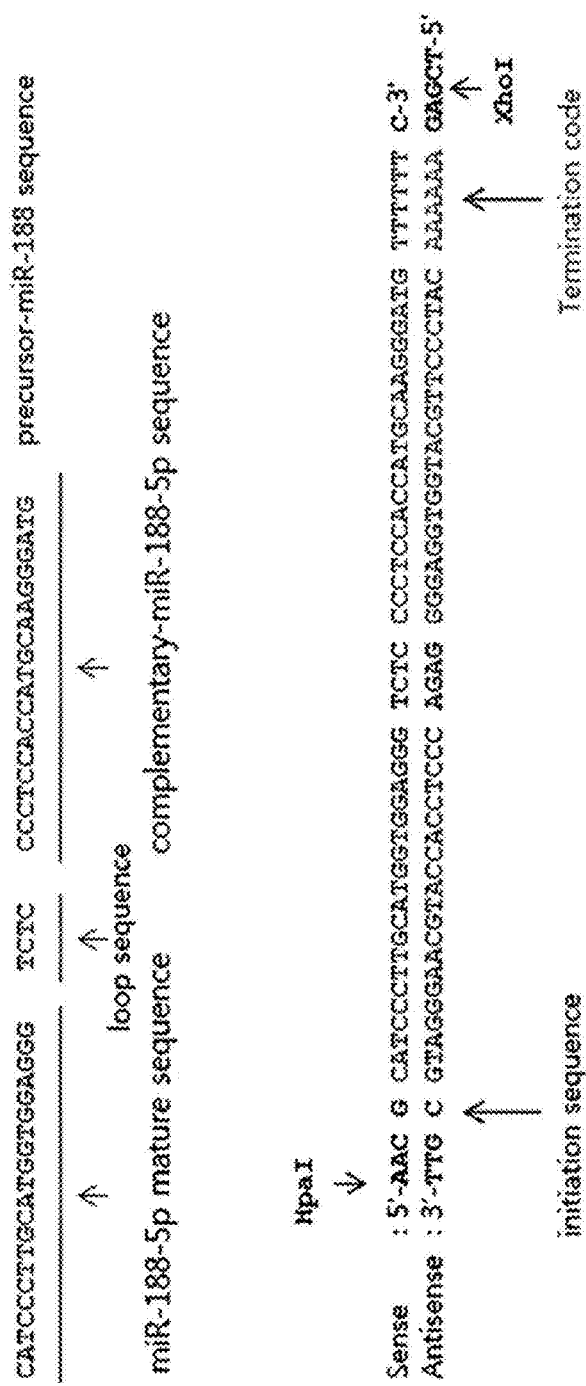
FIG. 8 shows the mature sequence of miR-188-5p and the loop sequence, complementary sequence, sense and antisense sequences of its pre-miRNA.

Because the role of CREB in synaptic plasticity has been well established, whether CREB is involved in the regulation of miR-188 expression was tested. Knockdown of Creb using small interfering CREB RNA (si-CREB) indeed resulted in significant down-regulation of mature miR-188-5p levels in rat primary hippocampal neurons (56.63±20.22%, p=0.017; FIG. 6c), suggesting that CREB can regulate miR-188-5p expression. Also, miR-188 promoter luciferase activity assay using rat primary hippocampal neuron cultures was performed. The miR-188 promoter activity was suppressed by CREB knockdown (37.03±10.66%, p=0.015; FIG. 6d) compared to control siRNAs. Taken together, these data suggest that LTP induction increases miR-188 levels potentially through CREB activation.

METHODS

1. Experimental Animals

All animal experimental procedures were approved by the Animal Care Committee of Seoul National University (Approval number: SNUIBC-080919-1). Transgenic mice with 5×FAD mutations were purchased from Jackson Laboratories (strain: B6SJL-Tg [APPSwFILon, PS1*M146L*L286V] 6799Vas/J) and maintained by crossing hemizygous transgenic mice with B6SJL F1 mice. And wildtype male C57BL/6 mice (25-30 g) were supplied by Koatech (Pyeongtaek, Korea). Animal treatment and maintenance were performed in accordance with the Animal Care and Use Guidelines of Seoul National University, Seoul, Korea.

2. Monomeric and Oligomeric $A\beta_{1-42}$ Preparation and BDNF Preparation

Monomeric and oligomeric Aβ were prepared as previously reported54,55. Synthetic $A\beta_{1-42}$ peptide (American Peptide, Sunnyvale, Calif., USA) was dissolved to 1 mM in 100% hexafluoroisopropanol (HFIP, Sigma Chemical Company, MO, USA). The solution was allowed to evaporate for 2 h in a Speed Vac (SPD2010, Thermo Savant, NY, USA). The resulting peptide film was stored at −20° C. or immediately resuspended in dimethyl sulfoxide (DMSO, Sigma Chemical Company) to produce a 1 mM solution. We used this for $mA\beta_{1-42}$ without any pre-cooling or freezing step. Then, to prepare oligomeric $A\beta_{1-42}$, this solution was diluted to 100 μM in phenol red-free Ham's F-12 medium (Life Technology, NY, USA) and incubated for 12 h at 4° C. Human recombinant BDNF was purchased from ProSpec-Tany TechnoGene (#CYT-207, Rehovot, Israel). Lyophilized BDNF was reconstituted using sterile water.

3. Primary Hippocampal Neuron Culture

Primary hippocampal neuron cultures were prepared from E18-19 pregnant Sprague-Dawley (SD) rats or from P1 5×FAD mice by dissociating with 0.25% trypsin and plated onto coverslips coated with poly-L-lysine. Neurons were grown in Neurobasal medium (Gibco, CA, USA) supplemented with B27 (Gibco, CA, USA), 2 mM GlutaMAX-I supplement (Gibco, CA, USA) and 100 μg/ml penicillin/streptomycin (Gibco, CA, USA) at 37° C. in a humidified environment of 95% $O_2$/5% $CO_2$.

4. DNA Constructs and Oligonucleotides

IRES-mGFP vector was a generous gift from Dr. A. L. Kolodkin, The Johns Hopkins University School of Medicine, Baltimore, Md. Expression vectors for miR-188-5p (miRbase Accession No. MIMAT0005301) were prepared by introducing synthesized oligonucleotides corresponding to the miR-188-5p sequences and complementary sequences into pLL3.7-DsRed2 vector. pLentiLox3.7 vector was used as the backbone vector, and the preparation method of the expression vector was as follows. 1) constructing pLL3.7-miR-188-EGFP vector using miR-188-5p and its complementary sequence to pLentiLox3.7 vector, 2) then, constructing pLL3.7-DsRed2 vector by removing EGFP of pLL3.7 vector and instead of it, cloning the part corresponding to DsRed2 of pIRES2-DsRed2 vector, and 3) constructing pLL3.7-miR-188-DsRed2 vector by cloning so as for DsRed2 to be inserted instead of EGFP of pLL3.7-miR-188-EGFP vector.

All constructs were sequenced using an ABI310 Sequencer. The oligonucleotide sequences used are as follows: the sequence of miR-188 mimic is 5'-CATCCCTTG-CATGGTGGAGGG-3'(synthesized on the basis of mmu miR-188-5p sequence; miRbase accession number MI0000230); miR-SC is 5'-CCUCGUGCCGUUC-CAUCAGGUAG-3'(SEQ ID NO: 5); miR-124 mimic is 5'-UAAGGCACGCGGUGAAUGCC-3' (SEQ ID NO: 6; synthesized on the basis of mmu miR-124-3p sequence; miRbase accession number MI0000828). The antisense 2'-O-methyl oligonucleotide (2'-O-Me-188-AS) to miR-188 was obtained from Integrated DNA Technologies (IDT, CA, USA) or Genolution Pharmaceuticals (Seoul, South Korea). The sequence of 2'-O-Me-188-AS is 5'-rGrCrUrCrGrCrCr-CrUrCrCrArCrCrArUrGrCmAmAmGmGmGmA-mUmGrUrGrArGrA-3' (SEQ ID NO: 7; r, RNA base; m, 2'-O-methyl base).

5. Human AD Brains

Paraffin-embedded brain stocks and the frozen tissues from 69 to 98 years old-AD and age-matched control subjects were obtained from the Netherlands Brain Bank (http://www.brainbank.nl/about-us/the-nbb/). Tissues from AD patients were diagnosed by neuropathological evidence using the criteria for Braak & Braak stage V or VI. The neuropathological diagnosis for non-demented controls consisted of the neuropathological criteria for classification as Braak & Braak stage 0 or 1. Coronal sections (4 μm) were cut through the hippocampus and processed for immunohistochemistry. For western blot analysis, frozen brain tissues were used. All experimental procedures were performed in accordance with 'the Guidelines of the Ethics Committee at Seoul National University'.

6. RT-qPCR.

Total RNA or specifically the small RNA fraction was extracted by miRNeasy Mini kit (cat no. 217004, Qiagen, CA, USA) or NucleoSpin microRNA kit (cat no. 740971, Macherey-Nagel, Duren, Germany), and 0.5-1.0 μg RNA was processed for cDNA synthesis using miScript PCR Starter Kit (cat no. 218193, Qiagen, CA, USA) according to the manufacturer's instructions.

To quantify the microRNA expression levels, SYBR Green microRNA assay-based RT-qPCR (using miScript PCR Starter Kit) was performed on a 7500 Fast Real-Time PCR systems (Applied Biosystems, CA, USA), using the ΔΔCt method. ROX was utilized as an endogenous reference to standardize the microRNA expression levels. All of the data were normalized by the snRNA RNU6B or 5S rRNA.

For reference, primers for miR-188-5p (cat no. MS00001757, miScript Primer Assays), miR-188-3p (cat no. MS00011312, miScript Primer Assays), and snRNA RNU6B (RNU6-2), provided to miScript PCR Starter Kit, were obtained from Qiagen (CA, USA). Primers for pri-miR-188 (SEQ ID NO: 8: 5'-TGTGGC-TATCTTGCTGCCC-3', SEQ ID NO: 9: 5'-GAGTCAT-TCTCCTTCCCACC-3'), and primers for Nrp-2 (SEQ ID NO: 10: 5'-AGAAGCCCGCTGAGATCT-3', SEQ ID NO: 11: 5'-CTCTCTGTCAAAAATGGATAT-3') were obtained from Bioneer (Daejeon, South Korea).

7. Immunohistochemistry

Human AD or age-matched control brains were incubated in 10% neutral buffered formalin for 48 h and then dehydrated and embedded in paraffin. Prior to immunostaining, slides were deparaffinized by oven heating and immersion in xylene. After dehydration through graded alcohols and water, tissue slices were immunostained overnight with a primary antibody against Nrp-2 (Cell Signaling Technology, MA, USA) at 1:50, followed by Alexa Fluor 488-conjugated secondary antibodies (Molecular Probes, CA, USA) at 1:100 After three washes in permeabilization buffer and a wash in PBS, cells were mounted on microscope slides in mounting medium (DAKO, CA, USA). Confocal microscopy was performed using an LSM 510 (Carl Zeiss, Jena, Germany).

8. Western Blot

Whole cell lysates or hippocampi extract samples were electrophoresed on a denaturing 10-15% SDS-PAGE gels and transferred to PVDF membranes (Millipore, MA, USA). Each membrane was probed with primary antibodies; Nrp-2 (Cell Signaling Technology, MA, USA) at 1:2,000, GAPDH (Santa Cruz Biotechnology, TX, USA) at 1:5,000. After washing, the membrane was incubated for 1 h at room temperature with Goat anti-Rabbit IgG (H+L), HRP (Molecular Probes, NY, USA). The HRP signals were visualized using an enhanced chemiluminescent (ECL) substrate (Thermo Fisher Scientific, IL, USA).

9. Dendritic Spine Density Analysis

Primary hippocampal neuron cultures from SD rat (E18-19) were transfected with 3 μg-IRES-mGFP, and with or without pLL3.7-miR-188-IRES-DsRed plasmid in 18 mm Φ in 12-well plates. The number of dendritic spines was evaluated at DIV 18. Fluorescent images were acquired by confocal microscopy (LSM 510, Carl Zeiss, Jena, Germany) using identical settings for all samples. Spines were counted on 20-40 μm segments of secondary dendrites extending at least 40-80 μm beyond the cell body (soma). 3-4 segments from each neuron were quantified. Primary hippocampal neuron cultures (DIV 10-12) from wild-type and 5×FAD P1 mice were transfected with one of the following combinations: 1) IRES-mGFP control vector alone; or 2) IRES-mGFP control vector plus the miRNA mimic oligonucleotides. The number of dendritic spines was evaluated at DIV 18-20.

10. Whole-Cell Patch Clamp Studies

Whole cell voltage-clamp was performed with a Multi-Clamp 700B amplifier (Molecular Devices, CA, USA). The series resistance (10-30 MΩ) was monitored in all experiments. The membrane potential was held at −70 mV during the recording. The frequency and amplitude of the mEPSCs were analyzed with the Mini Analysis program (Synaptosoft, NJ, USA). The noise level was below 5 pA, and 7 pA and was typically used as the threshold for mEPSC events. Five minutes of representative mEPSC recordings were used to generate the cumulative distribution plot.

The experiment method for patch clamp studies is described in more detail as follows. For AMPAR-mediated mEPSC, the vector structure and microRNA mimic were co-transfected to the primarily cultured hippocampal neurons (DIV 10-12) using CalPhos Mammalian Transfection Kit (Clontech Laboratories, CA, USA. miR-124 is one of the most common microRNAs expressed in murine brain 54. Neurons (DIV 17-19) were placed in the recording chamber and were continuously over-dissolved (1.5 ml/min) with the bath solution comprising 127 mM NaCl, 5 mM KCl, 2 mM $MgCl_2$, 2 mM $CaCl_2$, 12 mM glucose, 10 mM HEPES, and 0.001 mM tetrodotoxin (aCSF) at pH 7.3-7.4 and 300-305 mOsm. The NMDA receptor antagonist D-aminophosphonovalerate (20 μM) and GABAA receptor antagonist picrotoxin (100 μM) were added to aCSF. The whole cell voltage-clamp was performed with MultiClamp 700B amplifier (Molecular Devices, CA, USA). The recording electrode (8-10 MΩ) was filled with the solution comprising 130 mM CsMeSO4, 8 mM NaCl, 0.5 mM EGTA, 10 mM HEPES, 2 mM MgATP, 10 mM phosphocreatine, 5 mM QX-314 and 0.1 mM NaGTP (adjusting to pH 7.2 with CsOH).

11. Hippocampal Slice Preparation and Chemical LTP Induction

Acute hippocampal slices were prepared from 4- to 5-week-old (90~110 g) male SD rat brains. Briefly, brains were rapidly removed and coronal brain slices (400 μm) containing the hippocampus, were cut on a Vibratome (Leica, Germany) in ice-cold aCSF [119 mM NaCl, 2.5 mM KCl, 1 mM $MgSO_4$, 2.5 mM CaCl2, 1.25 mM $NaH_2PO_4$, 26 mM $NaHCO_3$ and 10 mM glucose] that was bubbled with 95% O2/5% $CO_2$ and adjust to pH 7.4. After a 1.5 h recovery at 27° C., an individual slice was transferred to a submerged recording chamber and continuously superfused with oxygenated aCSF at a rate of 2.5-3 ml/min at 33±1° C. LTP was introduced as previously described, and was then recorded in basal bath solution for 2 h. Electrical stimulation intensity was normalized to the value of the basal fiber volley (FV) amplitude. Then, average responses (mean±SEM) were expressed as the percentage of basal fEPSP amplitude.

The specific experiment contents for the fEPSP were as follows. Traverse hippocampal fragments (400 μM thickness) were prepared in the ice frozen dissection buffer (mM unit: sucrose 213 having bubbles with 95% $O_2$/5% $CO_2$; $NaHCO_3$ 26; KCI 2.5; $NaH_2PO_4$ 1.25; D-glucose 10; Na-pyruvate 2; Na-ascorbate 1.3; $MgCl_2$ 3.5 and $CaCl_2$ 0.5) using Vibratome (VT1200s, Leica, Germany). The slices were restored in the normal artificial cerebrospinal fluid (aCSF) (mM unit: NaCl 125; $NaHCO_3$ 26; KCI 2.5; $NaH_2PO_4$ 1.25; D-glucose 10; $MgCl_2$ 1.3 and $CaCl_2$ 2.5) at 36° C. for 1 hour and then maintained at a room temperature. The fEPSP recording was performed by researchers for genotypes using MultiClamp 700B amplifier (Molecular Devices, CA, USA) and Digidata 1440A interface (Molecular Devices, CA, USA) in a blind state. The signals were filtered at 2.8 kHz and digitalized at 10 kHz. The resistance of the record pipette was 2-3 MΩ when filled with aCSF. The synaptic reaction was caused at 0.05 Hz with the aCSF-filled glass pipette (0.3-0.5 MΩ) located in stratum radiatum, and the stimulus strength was adjusted to yield ~40% of the maximal synaptic reaction. LTP was induced by four episodes (0.1 Hz) of theta burst stimulation (TBS). TBS consists of 10 trains (5 Hz) and each train consists of 4 pulses (100 Hz). The data were analyzed using Clampfit software (Molecular Devices, CA, USA) and a user-defined macro written for Igor (WaveMetrics).

12. Behavioral Tests

Animals used were 7-month-old adult male mice. Before testing, mice were habituated to the testing room for 1 h. The specific contextual fear conditioned experiment was as follows. Each scrambler was connected to the electron constant current shock source which was controlled through the interface connected to Windows 7. A digital camera was installed on ceiling of each chamber and video signals were sent to the same computer for analysis. During training, after placing a mouse in a conditioning chamber (13×13×25 cm) for 3 minutes (before shock) and adapting in the same chamber for 10 minutes one day before training, foot-shock (0.7 mA, 2 seconds) was repeated 3 times at intervals between experiments for 1 minute. Next day, the conditioned mouse was placed in the same chamber, and the "freezing" time was measured for 5 minutes. The conditional freezing was defined as motionless except for breathing motion. The total freezing time of the experiment period was expressed as a percentage.

13. T-Maze Test

The spontaneous alternation behavior was tested using a T-maze (length of starting and target stem—30 cm, width—15 cm, height—7 cm and midsection piece 7×7 cm). The test was conducted twice at an interval of 2 minutes. The mouse was placed at the starting point, and then both targets were freely selectable. As soon as the mouse entered one target point, the target point was blocked by the center divider, and the mouse was locked for 30 seconds at the selection point. Then, the mouse was sent back to its original pen. After completely washing the T-maze with 70% ethanol, the mouse was placed at the starting point again, allowing to freely select one of the target points. The main measurement method of the present test is the shift rate defined by the rate of the experiment result at which the shift occurs (at first left point and then right point or vice versa) divided by the total number of tests. 4 experiments in total were performed for 2 days (twice a day).

14. Luciferase Activity Assay

The 1992 bp rat miR-188 3'-UTR containing the putative cAMP responsive element was PCR-amplified from rat genomic DNA by using the forward 5'-tct-tacgcgtgctagccctggcattttaatttagctc-3'(SEQ ID NO: 12) and reverse 5'-ccggaatgccaagcttgtttgcctttacctgtcac-3'(SEQ ID NO: 13) primers and the DNA fragment was cloned into the Nhel and Hindil sites on the 5'end of the luc+gene on the pGL3-basic vector. Briefly, the primary hippocampal neurons were cotransfected with pGL3-miR-188-promoter vector or pGL3-basic vector, pRL-Tk Renilla luciferase reporter vector (Promega, WI, USA) and 20 nmol/L of small RNAs (Silencer Select pre-designed siRNA or Silencer Select Negative Control #1 siRNA, Ambion, Life Technologies, Carlsbad, Calif., USA) using Lipofectamine 3000 (Life Technologies). The luciferase activity was determined 72 h post transfection and the reporter assay was performed according to the manufacturer's protocol (Dual-Glo Luciferase Assay System, Promega). Firefly luciferase activity (mean±SEM) was normalized to renilla luciferase and expressed as a percentage of the control.

15. LDH Assay

Primary hippocampal neuron cultures from SD rat (E18-19) were plated in 24-well plates and incubated at 37° C. On DIV-17, the neurons were treated with vehicle or 5 μM oAβ. After the treatment for 24 h, the cell toxicity was assessed using the CytoTox 96 nonradioactive cytotoxicity assay kit (Promega, WI, USA) according to the manufacturer's protocol. Briefly, for quantitative analysis, a 50 μl aliquot was transferred from each well to a 96 well plate. Then, 50 μl of the reagent was added to each well, and the reactions were incubated for 30 min at room temperature in the dark. After adding 50 μl of stop solution to each well, the fluorescence intensity was measured at 492 nm. Absorbance was measured using a TECAN Infinite M200 plate reader (TECAN, Männedorf, Switzerland). The obtained values were normalized to those of the completely lysed control. All experiments were performed in biological triplicate.

16. Statistical Analysis

The data are represented as the means±standard error of the mean (SEM) values. Student's t-test, non-parametric Mann-Whitney U test and a one-way ANOVA using post-hoc comparisons (IBM SPSS Statistics 20, IL, USA) were used to determine statistical significance. The results were considered to be statistically significant if $p<0.05$.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for preventing or treating Alzheimer's disease comprising:
   administering an effective amount of a composition comprising miR-188-5p to a subject in need thereof.

2. The method according to claim 1, wherein the miR-188-5p consists of the sequence represented by SEQ ID NO: 1.

3. The method according to claim 1, wherein the miR-188-5p inhibits expression of Nrp2 mRNA into a protein.

4. The method according to claim 1, wherein the composition comprises a pre-miRNA (precursor) of miR-188-5p.

5. The method according to claim 4, wherein the sequence of the pre-miRNA of miR-188-5p consists of the sequence represented by SEQ ID NO: 4.

6. The method according to claim 1, wherein the composition comprises an expression vector containing a polynucleotide encoding miR-188-5p.

7. A method for restoring cognitive function related to Alzheimer's disease comprising:
   administering an effective amount of miR-188-5p to a subject in need thereof.

8. The method according to claim 7, wherein the miR-188-5p consists of the sequence represented by SEQ ID NO: 1.

9. The method according to claim 7, wherein the miR-188-5p inhibits expression of Nrp2 mRNA into a protein.

10. The method according to claim 7, wherein the composition comprises a pre-miRNA (precursor) of miR-188-5p.

11. The method according to claim 10, wherein the sequence of the pre-miRNA of miR-188-5p consists of the sequence represented by SEQ ID NO: 4.

12. The method according to claim 7, wherein the composition comprises an expression vector containing a polynucleotide encoding miR-188-5p.

* * * * *

SEQUENCE LISTING

<160> NUMBER OF SEQ ID NOS: 13

<210> SEQ ID NO 1
<211> LENGTH: 21
<212> TYPE: DNA
<213> ORGANISM: Artificial Sequence

```
<220> FEATURE:
<223> OTHER INFORMATION: miR-188-5p mature sequence

<400> SEQUENCE: 1
catcccttgc atggtggagg g                                           21

<210> SEQ ID NO 2
<211> LENGTH: 21
<212> TYPE: DNA
<213> ORGANISM: Artificial Sequence
<220> FEATURE:
<223> OTHER INFORMATION: complementary miR-188-5p sequence

<400> SEQUENCE: 2
ccctccacca tgcaagggat g                                           21

<210> SEQ ID NO 3
<211> LENGTH: 57
<212> TYPE: DNA
<213> ORGANISM: Artificial Sequence
<220> FEATURE:
<223> OTHER INFORMATION: miR-188-5p sense sequence

<400> SEQUENCE: 3
aacgcatccc ttgcatggtg gagggtctcc cctccaccat gcaagggatg ttttttc    57

<210> SEQ ID NO 4
<211> LENGTH: 61
<212> TYPE: DNA
<213> ORGANISM: Artificial Sequence
<220> FEATURE:
<223> OTHER INFORMATION: miR-188-5p antisense sequence

<400> SEQUENCE: 4
tcgagaaaaa acatcccttg catggtggag gggagaccct ccaccatgca agggatgcgt  60
t                                                                 61

<210> SEQ ID NO 5
<211> LENGTH: 23
<212> TYPE: RNA
<213> ORGANISM: Artificial Sequence
<220> FEATURE:
<223> OTHER INFORMATION: miR-SC sequence

<400> SEQUENCE: 5
ccucgugccg uuccaucagg uag                                         23

<210> SEQ ID NO 6
<211> LENGTH: 20
<212> TYPE: RNA
<213> ORGANISM: Artificial Sequence
<220> FEATURE:
<223> OTHER INFORMATION: miR-124 mimic sequence

<400> SEQUENCE: 6
uaaggcacgc ggugaaugcc                                             20

<210> SEQ ID NO 7
<211> LENGTH: 62
<212> TYPE: RNA
<213> ORGANISM: Artificial Sequence
<220> FEATURE:
<223> OTHER INFORMATION: 2'-O-Me-188-AS sequence

<400> SEQUENCE: 7
```

```
rgrcrurcrg rcrcrcrurc rcrarcrcra rurgrcmama mgmgmgmamu mgrurgrarg    60 ra                                                                  62

<210> SEQ ID NO 8
<211> LENGTH: 19
<212> TYPE: DNA
<213> ORGANISM: Artificial Sequence
<220> FEATURE:
<223> OTHER INFORMATION: pri-miR-188 primer

<400> SEQUENCE: 8
tgtggctatc ttgctgccc                                                19

<210> SEQ ID NO 9
<211> LENGTH: 20
<212> TYPE: DNA
<213> ORGANISM: Artificial Sequence
<220> FEATURE:
<223> OTHER INFORMATION: pri-miR-188 primer

<400> SEQUENCE: 9
gagtcattct ccttcccacc                                               20

<210> SEQ ID NO 10
<211> LENGTH: 18
<212> TYPE: DNA
<213> ORGANISM: Artificial Sequence
<220> FEATURE:
<223> OTHER INFORMATION: Nrp-2 primer

<400> SEQUENCE: 10
agaagcccgc tgagatct                                                 18

<210> SEQ ID NO 11
<211> LENGTH: 21
<212> TYPE: DNA
<213> ORGANISM: Artificial Sequence
<220> FEATURE:
<223> OTHER INFORMATION: Nrp-2 primer

<400> SEQUENCE: 11
ctctctgtca aaaatggata t                                             21

<210> SEQ ID NO 12
<211> LENGTH: 37
<212> TYPE: DNA
<213> ORGANISM: Artificial Sequence
<220> FEATURE:
<223> OTHER INFORMATION: miR-188 3'-UTR forward primer

<400> SEQUENCE: 12
tcttacgcgt gctagccctg gcattttaat ttagctc                            37

<210> SEQ ID NO 13
<211> LENGTH: 35
<212> TYPE: DNA
<213> ORGANISM: Artificial Sequence
<220> FEATURE:
<223> OTHER INFORMATION: miR-188 3'-UTR reverse primer

<400> SEQUENCE: 13
ccggaatgcc aagcttgttt gcctttacct gtcac                              35
```